US012635884B2

(12) United States Patent
Yamashita et al.

(10) Patent No.: US 12,635,884 B2
(45) Date of Patent: May 26, 2026

(54) IMAGE FORMING APPARATUS

(71) Applicant: Tamron Co., Ltd., Saitama (JP)

(72) Inventors: Naoki Yamashita, Saitama (JP); Akira Onoda, Saitama (JP); Toshiya Segawa, Saitama (JP)

(73) Assignee: Tamron Co., Ltd., Saitama (JP)

( * ) Notice: Subject to any disclaimer, the term of this patent is extended or adjusted under 35 U.S.C. 154(b) by 0 days.

(21) Appl. No.: 18/918,092

(22) Filed: Oct. 17, 2024

(65) Prior Publication Data

US 2025/0152009 A1　　May 15, 2025

(30) Foreign Application Priority Data

Nov. 10, 2023　　(JP) ................................. 2023-192555
Aug. 1, 2024　　(JP) ................................. 2024-125852

(51) Int. Cl.
A61B 5/00 (2006.01)

(52) U.S. Cl.
CPC .... A61B 5/0071 (2013.01); A61B 2560/0443 (2013.01); A61B 2562/0233 (2013.01); A61B 2576/00 (2013.01)

(58) Field of Classification Search
CPC .......... A61B 5/0071; A61B 2560/0443; A61B 2562/0233; A61B 2576/00
See application file for complete search history.

(56) References Cited

U.S. PATENT DOCUMENTS

| | | | |
|---|---|---|---|
| 2006/0052710 A1* | 3/2006 | Miura .................. | A61B 1/0646 |
| | | | 600/476 |
| 2006/0264761 A1* | 11/2006 | Knoche ............... | A61B 5/0059 |
| | | | 600/476 |
| 2019/0079010 A1* | 3/2019 | Bawendi .............. | A61B 5/0071 |
| 2019/0170647 A1* | 6/2019 | Ikenaga ............... | A61B 1/0638 |
| 2021/0381960 A1* | 12/2021 | Na ........................ | G01S 7/4816 |

FOREIGN PATENT DOCUMENTS

| | | | |
|---|---|---|---|
| JP | 2018017675 A | * | 2/2018 |
| JP | 2019-510220 A | | 4/2019 |
| WO | WO 2017/018126 A1 | | 2/2017 |

* cited by examiner

*Primary Examiner* — Kaitlyn E Sebastian
(74) *Attorney, Agent, or Firm* — Paratus Law Group, PLLC

(57) ABSTRACT

In an image forming apparatus (1), an excitation light source (10) irradiates an object with excitation light for a first fluorescence substance and excitation light for a second fluorescence substance, a notch filter (20) transmits fluorescence in a wavelength range specific to each fluorescence substance among return light from the object, an imaging unit (30) separately captures images of the fluorescence in respective wavelength ranges, and an image processing unit (40) superimposes these images.

8 Claims, 20 Drawing Sheets

WAVELENGTH (nm)

*FIG. 20*

IMAGE FORMING APPARATUS

CROSS-REFERENCE TO RELATED APPLICATIONS

This application is based on and claims the benefit of priority from Japanese Patent Application No. 2023-192555, filed on Nov. 10, 2023, and Japanese Patent Application No. 2024-125852, filed on Aug. 1, 2024, the entire contents of which are incorporated herein by reference.

BACKGROUND OF THE INVENTION

Technical Field

The present invention relates to an image forming apparatus.

Related Art

Fluorescence imaging is known as a medical observation system that identifies the presence or absence of a tumor or the position of a tumor in a living tissue. Fluorescence imaging is a technique in which a fluorescence reagent is administered into a living body to be specifically accumulated in a tumor or the like in the living body, then the fluorescence reagent is excited by light of a specific wavelength, and fluorescence emitted by the fluorescence reagent is imaged to display an image. As described above, by detecting fluorescence in a living body, it is possible to grasp the presence or absence and the position of a tumor.

As a medical observation system, a technique is known in which indocyanine green (hereinafter, also referred to as "ICG"), which is a fluorescence substance, is administered into a living body, and the ICG is irradiated with excitation light to visualize and label ICG fluorescence in the near infrared range generated in response to the excitation light. Furthermore, as a technology for imaging fluorescence by a fluorescence reagent, a technology related to an endoscope, in which near infrared (also referred to as "NIR") fluorescence (800 to 850 nm) of ICG and fluorescence (680 to 740 nm) of methylene blue (also referred to as "MB") are detected by one image sensor is known (see, for example, WO 2017/018126 A). In addition, as a technology for imaging fluorescence by a fluorescence reagent, a technology related to a fluorescence observation system in which only short wave infrared (also referred to as "SWIR") fluorescence (900 to 2000 nm) of ICG is detected is known (see, for example, JP 2019-510220 A).

It is difficult to identify a plurality of locations in a living body with a label using ICG alone because of a monochromatic image. In the technique described in WO 2017/018126 A, in addition to ICG, multicolor fluorescence imaging using pharmaceutically approved MB has been attempted. However, the fluorescence spectrum of MB partially overlaps the fluorescence spectrum of ICG (see FIG. 2 below). Therefore, in the fluorescence imaging using the vicinity (800 to 850 nm) of the peak wavelength of the fluorescence of ICG, fluorescence of MB of 800 nm or more is also detected in the image sensor for ICG, and it may be difficult to identify an image of the fluorescence of ICG with an image of the fluorescence of MB.

An object of an aspect of the present invention is to provide a technique for identifiably detecting images of fluorescence of two kinds of fluorescence substances.

SUMMARY OF THE INVENTION

In order to solve the above problem, an image forming apparatus according to an aspect of the present invention includes an excitation light source configured to irradiate an object with excitation light for a first fluorescence substance and excitation light for a second fluorescence substance, an optical filter unit configured to transmit, from light from the object, fluorescence in a first wavelength range including near infrared or short wave infrared of the first fluorescence substance and fluorescence in a second wavelength range including short wave infrared of the second fluorescence substance, an imaging unit configured to capture an image of fluorescence in the first wavelength range and an image of fluorescence in the second wavelength range that have transmitted through the optical filter unit, and an image processing unit configured to superimpose the image of the fluorescence in the first wavelength range and the image of the fluorescence in the second wavelength range in the imaging unit.

According to an aspect of the present invention, it is possible to distinguishably detect images of fluorescence of two kinds of fluorescence substances.

BRIEF DESCRIPTION OF THE DRAWINGS

FIG. 1 is a diagram schematically illustrating a configuration of an image forming apparatus according to the first embodiment of the present invention;

FIG. 4 is a diagram schematically illustrating a functional configuration of an image processing unit in the first embodiment of the present invention;

FIG. 20 is a diagram schematically illustrating a functional configuration of an image forming apparatus according to the seventh embodiment of the present invention;

DESCRIPTION OF THE EMBODIMENTS

Figure 2:
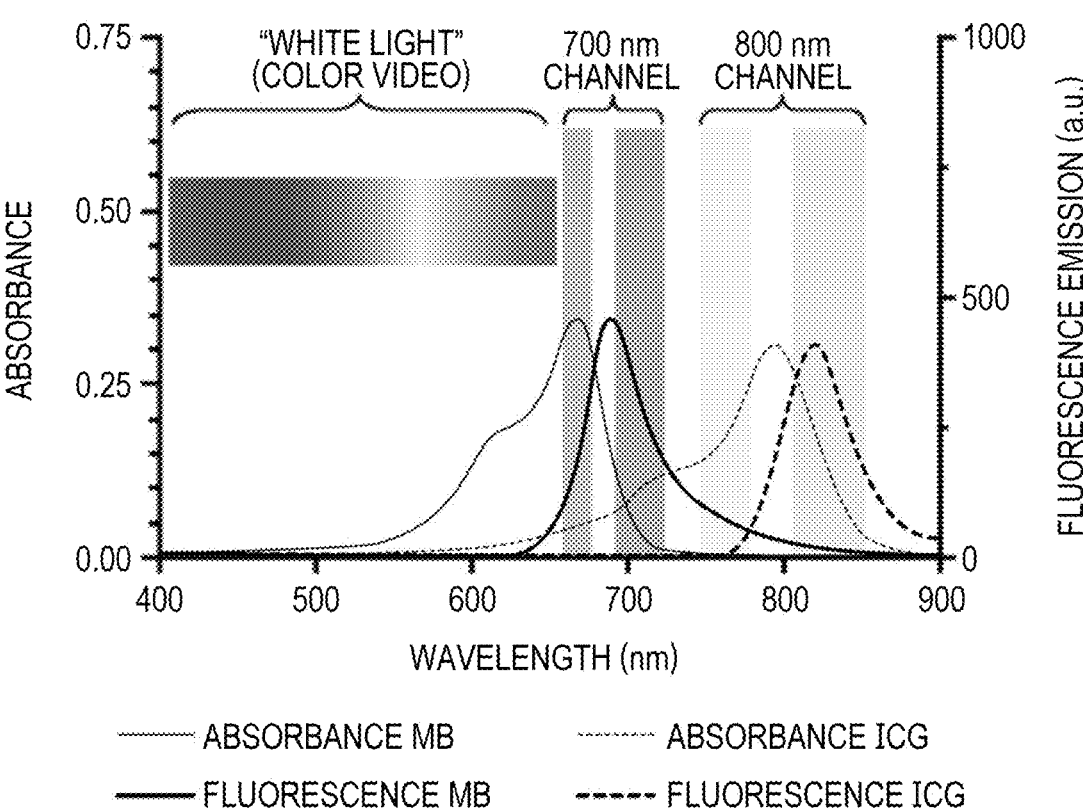
FIG. 2 is a diagram illustrating excitation spectra and fluorescence spectra of methylene blue (MB) as a first fluorescence substance and indocyanine green (ICG) as a second fluorescence substance in the first embodiment of the present invention.

The present invention enables further imaging using images of two kinds of fluorescence substances by detecting fluorescence in wavelength ranges that does not substantially overlap with each other for fluorescence of a first fluorescence substance and fluorescence of a second fluorescence substance to detect an image of each fluorescence substance.

In the present invention, the first fluorescence substance and the second fluorescence substance may be fluorescence substances in which only one of fluorescence of the first fluorescence substance and fluorescence of the second fluorescence substance is substantially detected in at least one of the wavelength range of fluorescence of the first fluorescence substance and the wavelength range of fluorescence of the second fluorescence substance. "Substantially detected" means, for example, a case where one of the first fluorescence substance and the second fluorescence substance does not emit fluorescence and the other emits fluorescence, or a case where both of the first fluorescence substance and the second fluorescence substance emit fluorescence, but there is a sufficient difference in intensity between fluorescence, and only one of the fluorescence can be detected.

In the present invention, unless otherwise specified, "near infrared" is a wavelength range located between visible light and short wave infrared, and means a wavelength range of 700 to 900 nm, for example. In the present invention, the "visible light" may be a wavelength range of 380 to 780 nm or any wavelength range included therein. "short wave infrared" means a wavelength range of 900 to 2500 nm. Further, in the present invention, "a first wavelength range including near infrared or short wave infrared" means that the first wavelength range overlaps at least partially with near infrared or short wave infrared, and "a second wavelength range including short wave infrared" means that the second wavelength range overlaps at least partially with short wave infrared.

Here, in the living body imaging as described above in the background art, a fluorescence substance that emits near infrared and short wave infrared fluorescence is suitably used. When the present invention is applied to living body imaging, two kinds of fluorescence substances in which at least one fluorescence wavelength range in which only one of fluorescence substances emitting fluorescence of one or both of near infrared and short wave infrared is substantially detected exists can be determined as the first fluorescence substance and the second fluorescence substance in the present invention.

In the present invention, it is possible to appropriately select an optical filter suitable for two kinds of fluorescence substances in which at least one fluorescence wavelength range in which only one of fluorescence substances emitting fluorescence of one or both of near infrared and short wave infrared is substantially detected exists from the fluorescence substances. In addition, the optical filter can be easily attached to and detached from an optical system of the image forming apparatus, and fluorescence of a plurality of fluorescence substances can be detected.

Hereinafter, the embodiments of the present invention will be described. The following embodiment is a form applied to living body imaging in which a first fluorescence substance that generates near infrared (NIR) fluorescence and a second fluorescence substance that generates short wave infrared (SWIR) fluorescence are used for fluorescent labeling. These fluorescence substances are respectively applied to the detection of different sites (e.g. a liver segment and a liver tumor) that may overlap in the same living tissue. The combinations of the first fluorescence substance and the second fluorescence substance in the following embodiments are illustrated in Table 1 below.

TABLE 1

| Embodiments | First fluorescence substance | Second fluorescence substance |
|---|---|---|
| 1 | MB | ICG |
| 2 | MB | FD-1080 |
| 3 | ICG | OTN ceramic probe Y |
| 4 | Cy5.5 | ICG |
| 5 | Cy5.5 | CH1055 |
| 6 | CH1055 (SWIR) | OTN ceramic probe Y |

The excitation wavelength, the maximum wavelength, and the excitation light wavelength range of the first fluorescence substance or the second fluorescence substance used in the following embodiments are illustrated in Table 2.

TABLE 2

| Fluorescence substance | Excitation wavelength (nm) | | Fluorescence wavelength (nm) | |
|---|---|---|---|---|
| | Maximum wavelength | Wavelength range | Maximum wavelength | Wavelength range |
| MB | 668 | 550-720 | 688 | 650-1200 |
| ICG | 805 | 600-900 | 835 | 750-1300 |
| FD-1080 | 1064 | 800-1100 | 1080 | 900-1400 |
| OTN ceramic probe Y | 980 | 920-1020 | 1530 | 1400-1650 |
| Cy5.5 | 685 | 550-740 | 706 | 660-850 |
| CH1055 | 750 | 600-900 | 1055 | 900-1350 |

First Embodiment

Figure 1:
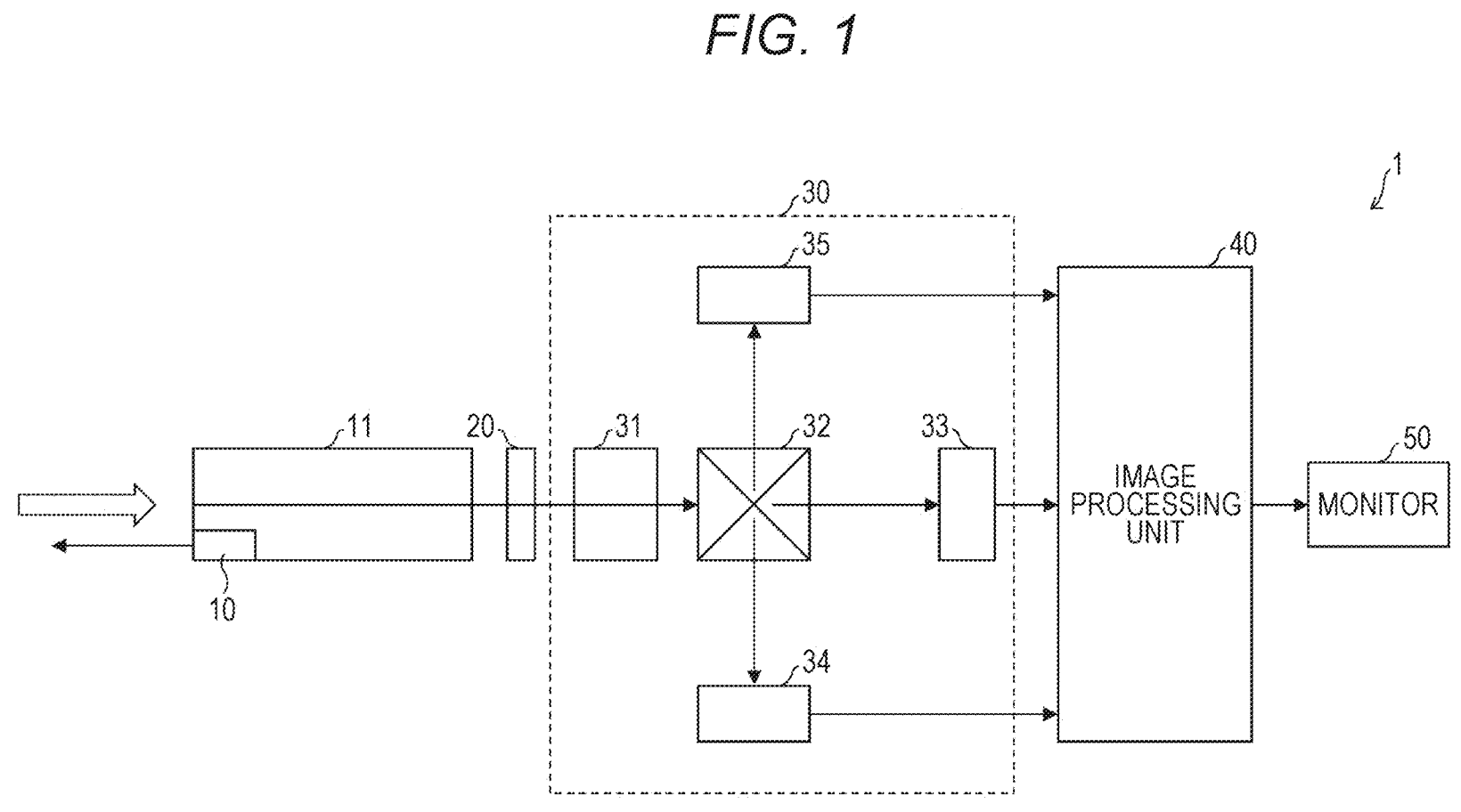

FIG. 1 schematically illustrates a configuration of an image forming apparatus according to the first embodiment of the present invention. The image forming apparatus of the present embodiment has an imaging function of an object to be observed by visible light and an imaging function of fluorescence emitted by excitation of each of MB and ICG administered to the object to be observed by radiation of excitation light such as near infrared light. As illustrated in FIG. 1, an image forming apparatus 1 includes an excitation light source 10, a notch filter 20, an imaging unit 30, an image processing unit 40, and a monitor 50.

[Excitation Light Source]

The excitation light source 10 is disposed at the distal end portion of a radiation probe 11 so as to irradiate the object to be observed with each of the excitation light for the first fluorescence substance (MB in the present embodiment) and the excitation light for the second fluorescence substance (ICG in the present embodiment).

The excitation light source 10 includes, for example, a first laser that generates light having a wavelength of 660 nm and a second laser that generates light having a wavelength of 808 nm. The first laser is a light source that generates MB excitation light, and the second laser is a light source that generates ICG excitation light. These lasers are configured to be able to independently adjust their outputs. Each of the first laser and the second laser may be configured to output light with a specific intensity, or may be configured to be capable of appropriately changing each output.

The excitation light source 10 independently controls the output of the first laser and the output of the second laser and irradiates the object to be observed with each excitation light. For example, the output of the second laser is set to be larger than the output of the first laser in consideration of a difference in intensity between fluorescence of MB in which fluorescence is detected in the wavelength range near the peak wavelength and fluorescence of ICG in which fluorescence is detected near the end of the fluorescence wavelength so that the SWIR fluorescence of the ICG is further enhanced.

The radiation probe 11 further includes a visible light source (not illustrated) at a distal end portion thereof. The visible light source is a light source for irradiating the object to be observed with visible light.

The radiation probe 11 is a portion to be inserted into the body of the test subject in a state where the MB and the ICG are administered in advance. The radiation probe 11 is, for example, a cylindrical object having a diameter of about 5 to 10 mm. The radiation probe 11 includes the excitation light source 10 and the visible light source at its distal end portion, and further includes an optical system. The optical system is, for example, an objective lens.

[Focus Shift Correction]

In the objective lens, a focus shift of light in a wavelength range (for example, 400 to 1700 nm) from visible light to short wave infrared light is corrected. For example, the objective lens is optically designed so as to reduce a deviation of back focus (BF) in the wavelength ranges of visible light, near infrared, and short wave infrared. The "back focus" (BF) is a distance from the surface of the optical system closest to the image to the focus position, and in the present embodiment, is a focus position on a paraxial ray (a ray passing through a height extremely close to the optical axis). The value of the focus position does not change even when F number of the lens changes.

From the viewpoint of favorably correcting the aberration of the image detected by each sensor, the objective lens preferably satisfies the following formula (1). In the following formulas, "BF_550 nm" represents back focus in the entire optical system of 550 nm, and "BF_850 nm" represents back focus in the entire optical system of 850 nm.

$$|BF\_550\ nm - BF\_850\ nm| < 0.03\ mm \tag{1}$$

The difference due to the presence or absence of the focus shift correction becomes more remarkable on the long wavelength side, and the deviation of the focus position on the long wavelength side is corrected to be larger (more effectively). Since the objective lens is subjected to the focus shift correction, the light projecting system can be made common to three types of image sensors of the light receiving system to be described later, and further, adjustment of the position of each image sensor according to the focus shift is reduced or unnecessary. Therefore, it is more preferable that the objective lens is subjected to the focus shift correction from the viewpoint of simplifying the optical design of the imaging unit 30.

The radiation probe 11 is detachably connected to the imaging unit 30 via the notch filter 20. In the image forming apparatus 1, the light received by the radiation probe 11 is guided to the imaging unit 30 via the notch filter 20. Such a configuration capable of guiding light is, for example, a configuration that realizes a method called relay lens or pupil relay that transmits an image by light in a relay form. Alternatively, the configuration is, for example, an optical fiber capable of transmitting image information, such as an image guide fiber.

[Notch Filter]

The notch filter 20 is an optical filter unit that transmits NIR fluorescence of MB and SWIR fluorescence of ICG among light from the object to be observed. As described above, in the present embodiment, the wavelength range (first wavelength range) of fluorescence of MB which is the first fluorescence substance is included in the NIR, and the wavelength range (second wavelength range) of fluorescence of ICG which is the second fluorescence substance is included in the SWIR.

Here, as illustrated in FIG. 2 (source: "FIG. 3" of "Image-Guided Surgery using Invisible Near-Infrared Light: Fundamentals of Clinical Translation", Mol Imaging. Author manuscript; available in PMC 2011 Oct. 1), MB has a peak of fluorescence intensity in NIR. ICG has fluorescence in NIR, but in the wavelength range near the peak wavelength of fluorescence of MB, the intensity of NIR fluorescence of ICG is sufficiently smaller than the intensity of NIR fluorescence of MB. On the other hand, ICG has SWIR fluorescence, but the intensity of SWIR fluorescence of MB is sufficiently lower than that of ICG, so that it can also be said that MB does not substantially have SWIR fluorescence relative to ICG. In addition, since MB is not excited at the wavelength of 808 nm of the second laser, the difference between the intensity of the SWIR fluorescence of ICG and the intensity of the SWIR fluorescence of MB can be further increased by increasing the output of the second laser, and the output of the second laser does not affect the SWIR intensity of MB. The notch filter 20 is designed to transmit light in a wavelength range in which a difference in intensity of the fluorescence is observed and to attenuate light in other wavelength ranges except for visible light.

Figure 3:
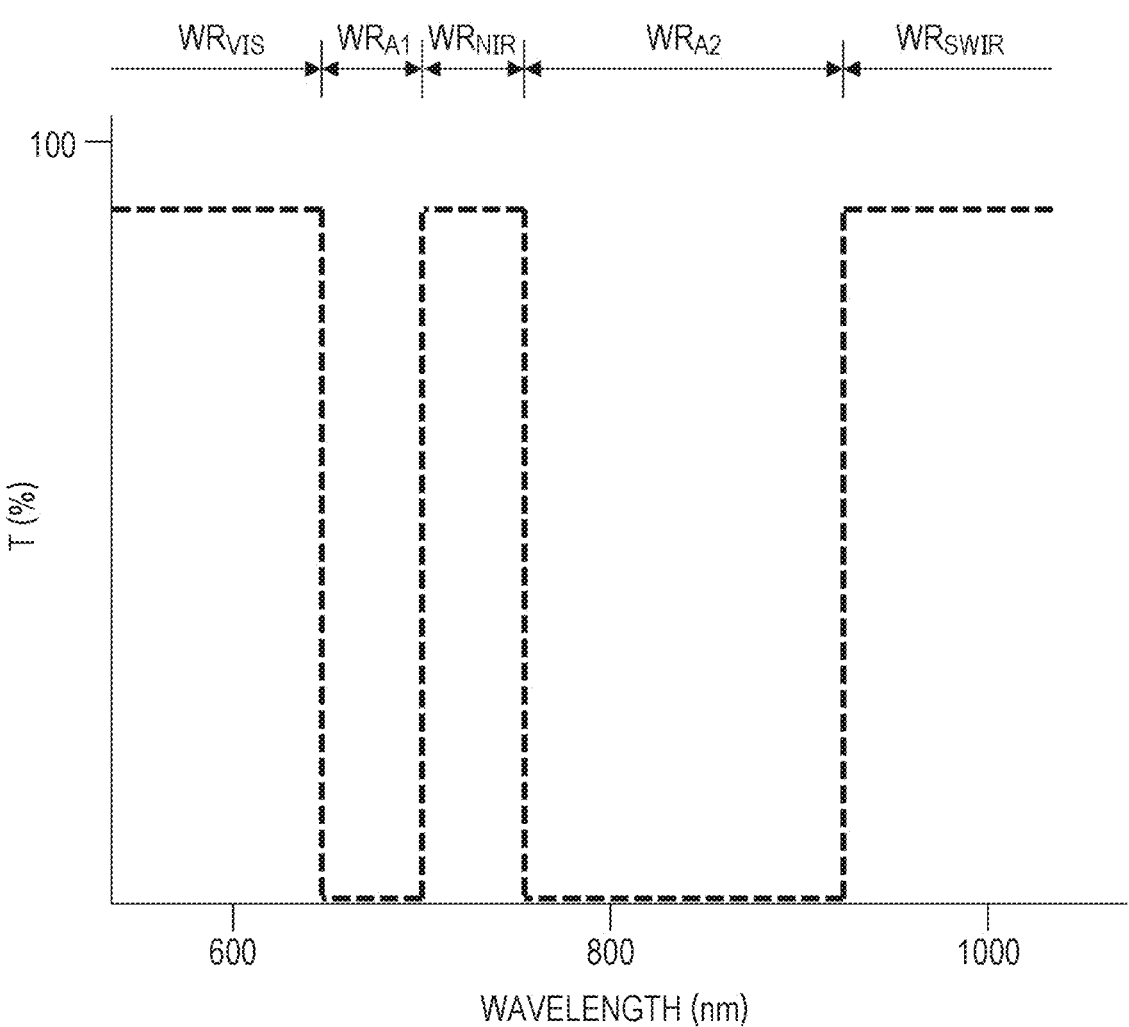
FIG. 3 is a diagram illustrating a transmission wavelength range and an attenuation wavelength range of the notch filter in the first embodiment of the present invention.

A transmission wavelength range and an attenuation wavelength range of notch filter 20 are illustrated in FIG. 3. As illustrated in FIG. 3, the notch filter 20 is designed to transmit light in a specific visible light wavelength range $WR_{VIS}$, NIR wavelength range $WR_{NIR}$, and SWIR wavelength range $WR_{SWIR}$, and attenuate light in a first attenuation wavelength range $WR_{A1}$ between $WR_{VIS}$ and $WR_{NIR}$ and light in a second attenuation wavelength range $WR_{A2}$ between $WR_{NIR}$ and $WR_{SWIR}$.

More specifically, in the wavelength range for transmitting light, $WR_{VIS}$ is 400 to 650 nm, $WR_{NIR}$ is 700 to 750 nm, and $WR_{SWIR}$ is 925 to 1300 nm. $WR_{VIS}$ is a wavelength range of visible light, $WR_{NIR}$ is a wavelength range of NIR fluorescence of MB, and $WR_{SWIR}$ is a wavelength range of SWIR fluorescence of ICG.

In a wavelength range in which light is attenuated, $WR_{A1}$ is 650 to 700 nm (OD (optical density)>6) and $WR_{A2}$ is 750 to 925 nm (OD>6 at 790 to 812 nm). $WR_{A1}$ includes a wavelength range of MB excitation light, and $WR_{A2}$ includes a wavelength range of ICG excitation light and a wavelength range of ICG NIR fluorescence.

As described above, the notch filter 20 is configured to attenuate light in a first attenuation wavelength range shorter than the first wavelength range and light in a second attenuation wavelength range longer than the first wavelength range and shorter than the second wavelength range. In addition, the notch filter 20 is configured to further transmit visible light among the light from the object to be observed in a wavelength range shorter than the first attenuation wavelength range.

Notch filter 20 attenuates light in a wavelength range longer than the wavelength of fluorescence with intensity of fluorescence in the first wavelength range in which intensity of fluorescence in the first wavelength range is larger than intensity of fluorescence in the second wavelength range. Therefore, since the influence of the fluorescence in the first wavelength range in the detection of the fluorescence in the second wavelength range can be reduced, it is advantageous from the viewpoint of enhancing the detection accuracy of the fluorescence in the second wavelength range.

Notch filter 20 is detachably disposed in image forming apparatus 1 on the optical path of fluorescence. Therefore, it is easily detachable and replaceable in the image forming apparatus 1. Therefore, optical filters corresponding to various fluorescence substances or different fluorescence wavelength ranges can be appropriately adopted, which is advantageous from the viewpoint of enhancing versatility of the image forming apparatus 1. Note that "detachable" includes not only a case where the user can easily attach and detach, but also a case where the user cannot easily disassemble. In the latter case, for example, a mechanism to which the notch filter 20 can be attached and detached is provided inside a waterproof mechanism, a protective cover, or the like.

[Imaging Unit]

The imaging unit 30 includes an image forming lens 31, a beam splitter 32, a near infrared sensor 33, a short wave infrared sensor 34, and a visible light sensor 35.

The image forming lens 31 is an optical element that focuses light (NIR fluorescence, SWIR fluorescence and visible light) from the notch filter 20 so as to form an image in each sensor. The image forming lens 31 is a lens capable of coping with visible light to short wave infrared light, and its transmission band is, for example, 400 to 1700 nm.

Similarly to the objective lens described above, the image forming lens 31 is also subjected to focus shift correction. The image forming lens 31 preferably satisfies the following formula (2) from the viewpoint of favorably correcting the aberration of the image detected by each sensor. In the following formula, "BF_1600 nm" represents back focus in the entire optical system of 1600 nm.

$$|BF\_550\ nm - BF\_1600\ nm| < 0.05\ mm \tag{2}$$

Since the focus shift correction is performed on the image forming lens 31, it is not necessary to adjust the positions of the three types of image sensors in the imaging unit 30. Therefore, it is more preferable that the focus shift correction is performed on the image forming lens 31 from the viewpoint of simplifying the optical design of the imaging unit 30. For example, as the image forming lens 31, a focus shift corrected lens having a focal length of 24 mm, an F number of 5.5, BF_550 nm of −0.015 mm, BF_850 nm of 0.008 mm, and BF_1600 nm of 0.028 mm can be used.

The beam splitter 32 is a beam splitter that divides light in the wavelength range of the transmitted light set by the notch filter 20 into different directions, and is, for example, a cubic beam splitter having two types of optical thin films orthogonal to each other. Of the light that has passed through the notch filter 20 and the image forming lens 31, the beam splitter 32 guides visible light (400 to 650 nm) in one direction orthogonal to the incident direction, guides short wave infrared (925 to 1700 nm) in the other direction orthogonal to the incident direction, and transmits (straightly advances) near infrared (700 to 880 nm).

The positions on the optical paths of the near infrared sensor 33, the short wave infrared sensor 34, and the visible light sensor 35 are each adjusted to a position where the focus position is the position of the sensor (image plane) according to the wavelength of each component of light (VIS, NIR, and SWIR light) received by each sensor.

The near infrared sensor 33 is an image sensor that exposes incident light and outputs an image signal obtained by photoelectrically converting the exposed light, and is a monochrome image sensor having sensitivity to near infrared. The near infrared sensor 33 is, for example, an image sensor having sensitivity in a wavelength range of 400 to 1000 nm. The near infrared sensor 33 outputs a signal of a received NIR light image (NIR image).

The short wave infrared sensor 34 is an image sensor that exposes incident light and outputs an image signal obtained by photoelectrically converting the exposed light, and is a monochrome image sensor having sensitivity to short wave infrared. The short wave infrared sensor 34 is an image sensor having sensitivity in a wavelength range of 400 to 1700 nm, for example. The short wave infrared sensor 34 outputs a signal of a received SWIR light image (SWIR image).

The visible light sensor 35 is an image sensor that exposes incident light and outputs an image signal obtained by photoelectrically converting the exposed light, and is an image sensor having sensitivity in a wavelength range of visible light. The visible light sensor 35 is, for example, an image sensor having sensitivity in a wavelength range of 400 to 1000 nm. In the visible light sensor 35, color filters of three primary colors of red (R), green (G), and blue (B), or cyan (C), magenta (M), and yellow (Y) are arranged in a Bayer array or a honeycomb array on an image plane. The visible light sensor 35 outputs a signal of a received visible light image (VIS image).

As described above, the imaging unit 30 is configured to capture each of an image of the NIR fluorescence and an image of the SWIR fluorescence transmitted through the notch filter 20. In addition, the imaging unit 30 is configured to further capture an image of visible light transmitted through the notch filter 20.

[Image Processing Unit]

Figure 4:
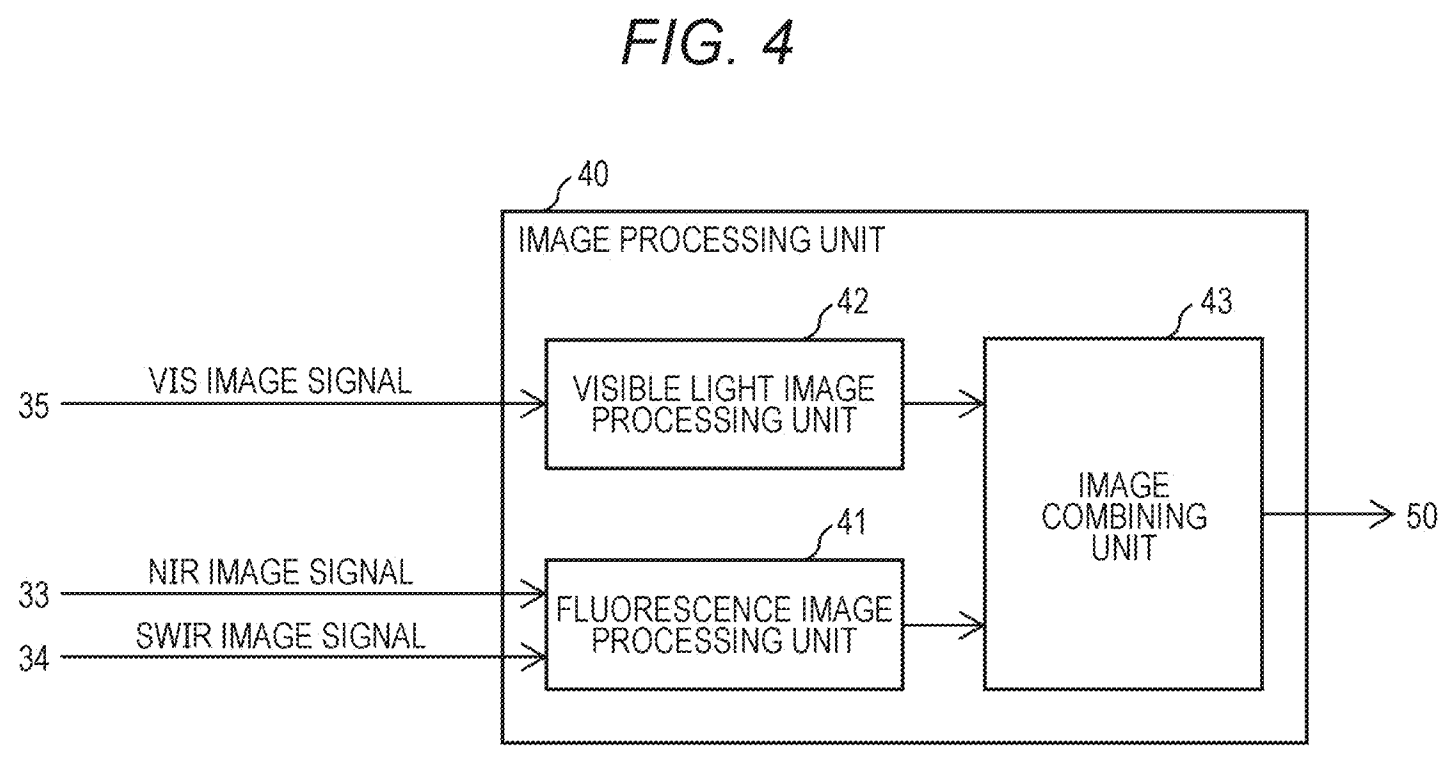

The image processing unit 40 superimposes the NIR image and the SWIR image in the imaging unit 30. In addition, the image processing unit 40 further superimposes the VIS image in the imaging unit 30 on the NIR image and the SWIR image. FIG. 4 schematically illustrates an example of a functional configuration of the image processing unit 40.

The image processing unit 40 includes a fluorescence image processing unit 41, a visible light image processing unit 42, and an image combining unit 43.

To the fluorescence image processing unit 41, a signal of an NIR image (an image of NIR fluorescence of MB) is input from the near infrared sensor 33, and a signal of a SWIR image (an image of SWIR fluorescence of ICG) is input from the short wave infrared sensor 34. The fluorescence image processing unit 41 performs predetermined image processing suitable for the fluorescence image on the signal of the input fluorescence image and outputs the processed signal. For example, the fluorescence image processing unit 41 processes the NIR image and the SWIR image into images of different colors that can be identified.

A signal of a VIS image (image of visible light to be observed) is input from the visible light sensor 35 to the visible light image processing unit 42. The visible light image processing unit 42 performs predetermined image processing suitable for the visible light image on the input signal of the visible light image and outputs the processed signal.

A signal of the processed fluorescence image is input from the fluorescence image processing unit 41 and a signal of the processed visible light image is input from the visible light image processing unit 42 to the image combining unit 43. For example, the image combining unit 43 performs processing of combining the processed fluorescence images with the processed visible light image.

The image processing unit 40 transmits a signal of the composite image combined by the image combining unit 43 to the monitor 50. The monitor 50 displays an image input from the image processing unit 40, and the monitor 50 is, for example, a display device such as a liquid crystal display (LCD).

[Image Formation]

Figure 5:
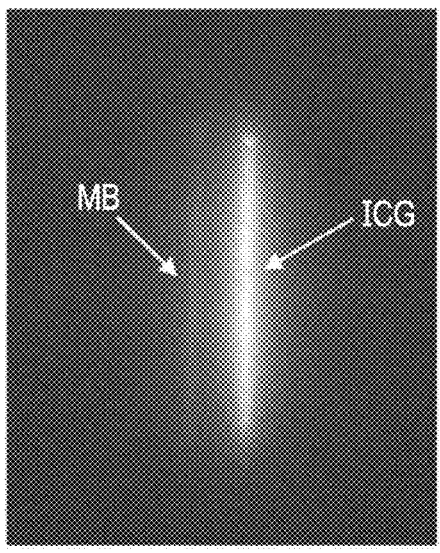
FIG. 5 is a diagram illustrating a photograph of an example of an image of fluorescence in a first wavelength range obtained by the image forming apparatus according to the first embodiment of the present invention.
Figure 6:
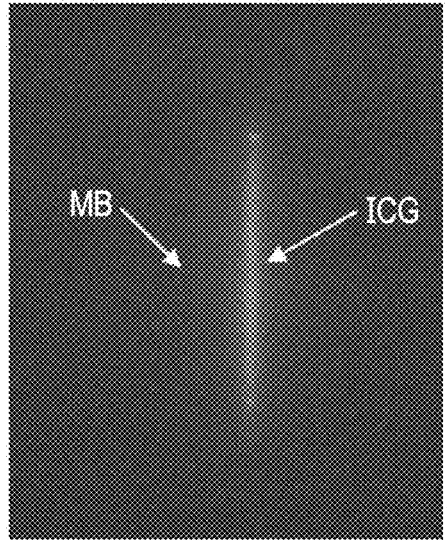
FIG. 6 is a diagram illustrating a photograph of an example of an image of fluorescence in a second wavelength range obtained by the image forming apparatus according to the first embodiment of the present invention.

FIG. 5 is a diagram illustrating a photograph of an example of an NIR image obtained by the image forming apparatus 1, and FIG. 6 is a diagram illustrating a photograph of an example of a SWIR image obtained by the image forming apparatus 1. Each of the photographs of FIGS. 5 and 6 is a photograph of an image when an object to be observed example in which a glass capillary tube (MB capillary tube) sealing the MB solution and a glass capillary tube (ICG capillary tube) sealing the ICG solution are arranged and a 1.5 mm-thick roast ham is placed thereon is observed. The object to be observed example imitates a living tissue in which a fluorescence substance is fixed in blood vessels close to each other but different from each other. In addition, an arrow in the drawing indicates the position of the image of the test body.

The excitation light source 10 irradiates the object to be observed with the excitation light for MB and the excitation light for ICG and the visible light at substantially the same time from the first laser and the second laser. Note that "irradiate at substantially the same time" means not only a case where the light radiation periods completely coincide with each other but also a case where the light radiation periods partially overlap with each other.

When the object to be observed example is irradiated with the first laser (light having a wavelength of 660 nm), the excitation efficiency of MB is maximized, and the MB capillary tube emits near infrared fluorescence having a maximum fluorescence wavelength of about 690 nm. In addition, since ICG having a maximum excitation wavelength of around 808 nm is also excited by being irradiated with excitation light having a wavelength of 660 nm, the ICG capillary tube also emits near infrared fluorescence having a maximum fluorescence wavelength of around 835 nm. By irradiating the object to be observed example with the first laser in this manner, the near infrared sensor 33 detects a signal of the NIR image including the image of the MB capillary tube and the image of the ICG capillary tube as illustrated in FIG. 5. As the NIR image, an NIR image as illustrated in FIG. 5 is obtained.

When the object to be observed example is irradiated with the second laser (light having a wavelength of 808 nm), the excitation light factor of ICG is maximized, and the ICG capillary tube emits SWIR fluorescence together with NIR fluorescence. On the other hand, MB is not substantially excited in the wavelength range of the second laser. Therefore, the short wave infrared sensor 34 detects a signal of the SWIR image of the ICG capillary tube as illustrated in FIG. 6.

By performing processing of superimposing the signal of the NIR image and the signal of the SWIR image in the image combining unit 43, a signal of a fluorescence composite image in which both the image of the MB capillary tube and the image of the ICG capillary tube are clearly displayed is obtained.

On the other hand, when the object to be observed example is irradiated with visible light (for example, light having a wavelength of 400 to 650 nm) from a visible light source, the visible light sensor 35 detects a signal of a color VIS image of the object to be observed example. When the image combining unit 43 performs the processing of further superimposing the signal of the above fluorescence composite image on the signal of the VIS image, a signal of a composite image in which the image of the NIR fluorescence of the MB capillary tube and the image of the SWIR fluorescence of the ICG capillary tube are superimposed in the color image of the object to be observed example is obtained.

Figure 7:
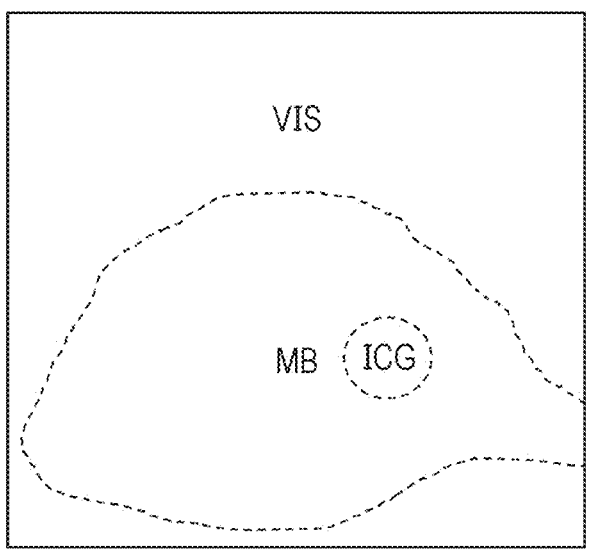
FIG. 7 is a diagram schematically illustrating an example of a composite image obtained by superimposing an image of fluorescence in a first wavelength range and an image of fluorescence in a second wavelength range obtained by the image forming apparatus according to the first embodiment of the present invention on an image of visible light.

Therefore, when MB is used as a fluorescent labeling reagent for a liver segment, ICG is used as a fluorescent labeling reagent for a liver tumor, and the entire liver is irradiated with excitation light by the image forming apparatus 1, an image as illustrated in FIG. 7 is formed. FIG. 7 is a diagram schematically illustrating an example of a composite image formed by the image forming apparatus 1. For example, when the entire liver is irradiated with excitation light during an operation, a composite image in which an NIR fluorescence image of MB spreading in the liver segment and a SWIR fluorescence image of ICG are superimposed on a color VIS image of the entire liver is displayed on the monitor 50 in real time. The NIR fluorescence image of MB is, for example, a light green image in which the VIS image is visible and which is easily distinguished from the VIS image. The SWIR fluorescence image of ICG is, for example, a blue to purple image in which the VIS image is visible and which is easily distinguished from the NIR fluorescence image of MB.

The color display of the VIS image may be adjusted by a color filter disposed in the visible light sensor 35. The colors of the NIR fluorescence image of MB and the SWIR fluorescence image of ICG can be arbitrarily set by the fluorescence image processing unit 41. Therefore, according to the image forming apparatus 1, even if two kinds of fluorescence substances having overlapping fluorescence wavelength ranges are used, the sites labeled with the respective fluorescence substances can be clearly and distinguishably displayed in the living body imaging in which the sites detected by fluorescence can overlap. The image forming apparatus 1 can be used for laparotomy, but can also be applied to a laparoscope in laparoscopic surgery.

In the embodiment of the present invention, an example of a rigid endoscope system such as a laparoscope has been described, but application to other than an endoscope is naturally possible. When the system is used with the radiation probe 11 of FIG. 1 removed, it can also be used as an exoscope. As in the present invention, considering that the notch filter can be easily attached to and detached from the optical system of the image forming apparatus and can cope with a plurality of fluorescence reagents, it is more preferable to use the notch filter for an exoscope as compared with an endoscope in which sterilization of the entire apparatus is required and airtightness is emphasized. Note that, in the case of application to an endoscope, the notch filter attachment/detachment portion is sealed by sealing or the like to improve airtightness and prevent foreign matter from entering the inside, whereby the filter can be suitably used for the endoscope.

Second Embodiment

Hereinafter, another embodiment of the present invention will be described. In the embodiment described later, for convenience of description, members having the same functions as the members described in the above embodiment are denoted by the same reference numerals, and the description thereof will not be repeated.

The present embodiment is a mode for using MB as the first fluorescence substance and using FD-1080 as the second fluorescence substance. The image forming apparatus of the present embodiment is substantially the same as that of the first embodiment described above except that the wavelength of the light of the second laser in the excitation light source and the transmitted light wavelength range and the attenuated light wavelength range in the notch filter are different.

Figure 8:
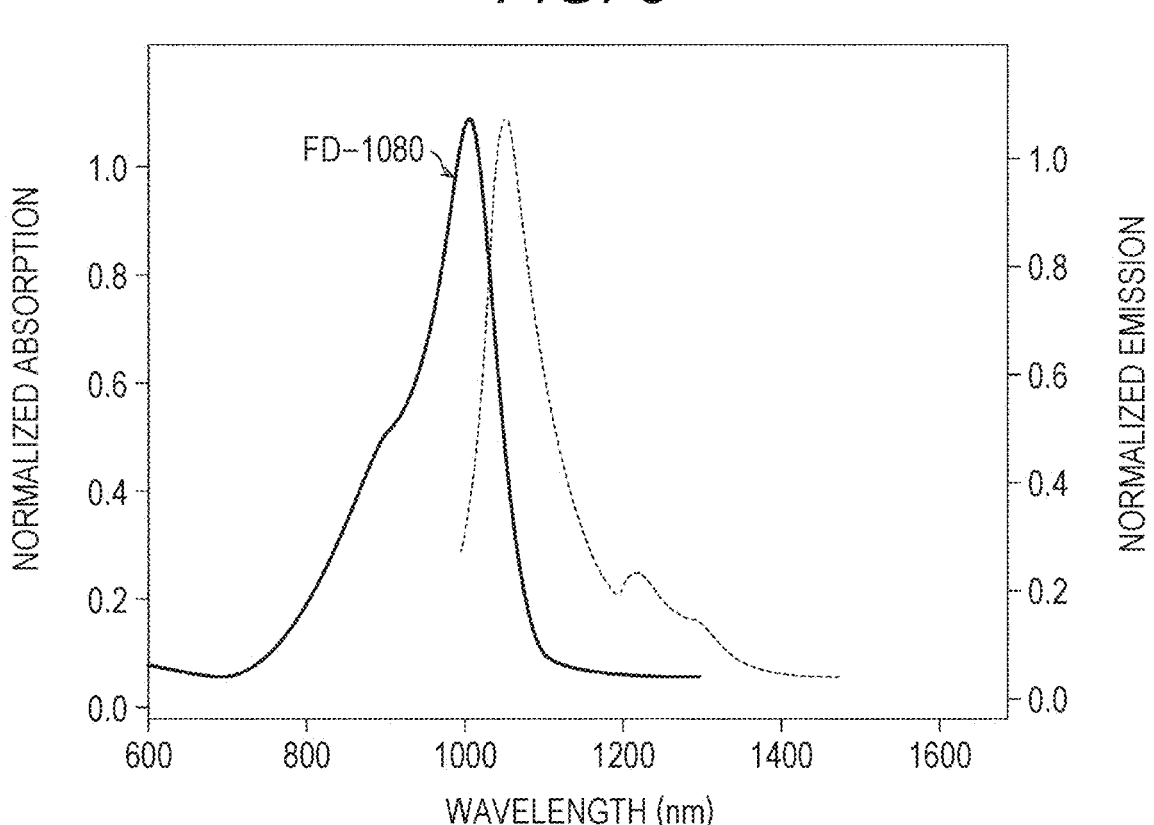
FIG. 8 is a diagram illustrating an excitation spectrum and a fluorescence spectrum of a cyanine dye (FD-1080) which is a second fluorescence substance in the second embodiment of the present invention.

FIG. 8 (source: FIG. 1b of "J-aggregates of Cyanine Dye for NIR-II In-vivo Dynamic Vascular Imaging Beyond 1500 nm", Journal of the American Chemical Society, November 2019) illustrates an excitation spectrum (solid line) and a fluorescence spectrum (dotted line) of FD-1080 which is the second fluorescence substance in the present embodiment. FD-1080 is a kind of cyanine dye. The maximum wavelength of the excitation wavelength of FD-1080 is 1064 nm, and the wavelength range of the fluorescence wavelength is 900 to 1400 nm.

The second laser in the present embodiment is a laser that generates light having a wavelength of 1064 nm.

Figure 9:
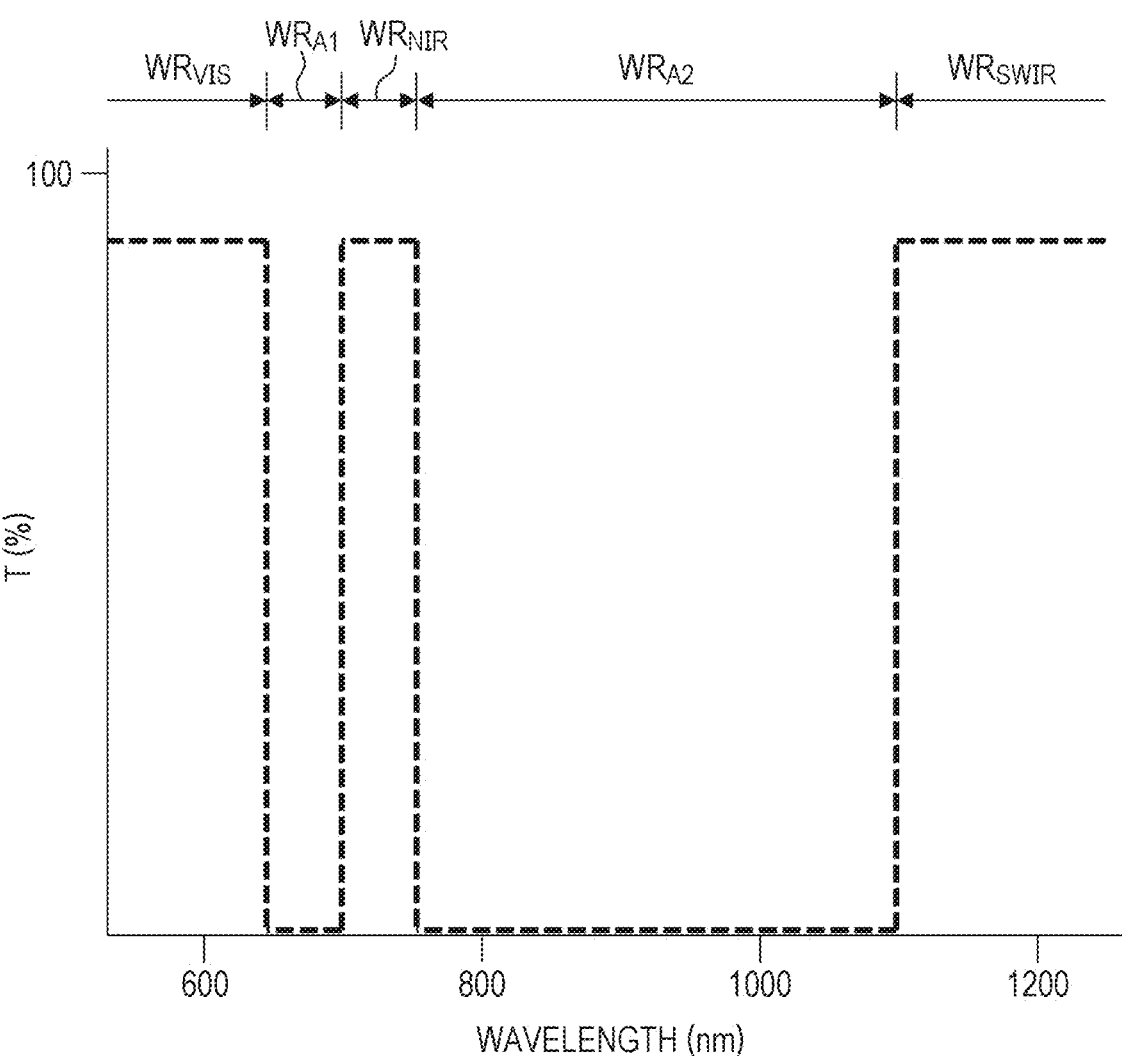
FIG. 9 is a diagram illustrating a transmission wavelength range and an attenuation wavelength range of a notch filter in the second embodiment of the present invention.

FIG. 9 illustrates a transmission wavelength range and an attenuation wavelength range of the notch filter in the present embodiment. The wavelength range in which the notch filter transmits light is such that $WR_{VIS}$ is 400 to 650 nm, $WR_{NIR}$ is 700 to 750 nm, and $WR_{SWIR}$ is 1100 to 1400 nm. In the wavelength range in which the notch filter attenuates light, $WR_{A1}$ is 650 to 700 nm and $WR_{A2}$ is 750 to 1100 nm.

In the present embodiment, a composite image in which an image of NIR fluorescence of MB and an image of SWIR fluorescence of FD-1080 are superimposed on a color VIS image can be formed. As described above, according to the present embodiment, as in the first embodiment, it is possible to detect fluorescence images of two kinds of fluorescence substances in an identifiable manner. Therefore, as in first embodiment described above, even when two kinds of fluorescence substances having overlapping fluorescence wavelength ranges are used, in living body imaging in which sites detected by fluorescence can overlap, the sites labeled with the respective fluorescence substances can be clearly and distinguishably displayed.

Third Embodiment

In the present embodiment, ICG is used as the first fluorescence substance, and OTN ceramic probe Y is used as the second fluorescence substance. The image forming apparatus of the present embodiment is substantially the same as that of the first embodiment described above except that the wavelengths of the light of the first laser and the second laser in the excitation light source and the transmitted light wavelength range and the attenuated light wavelength range in the notch filter are different.

Figure 10:
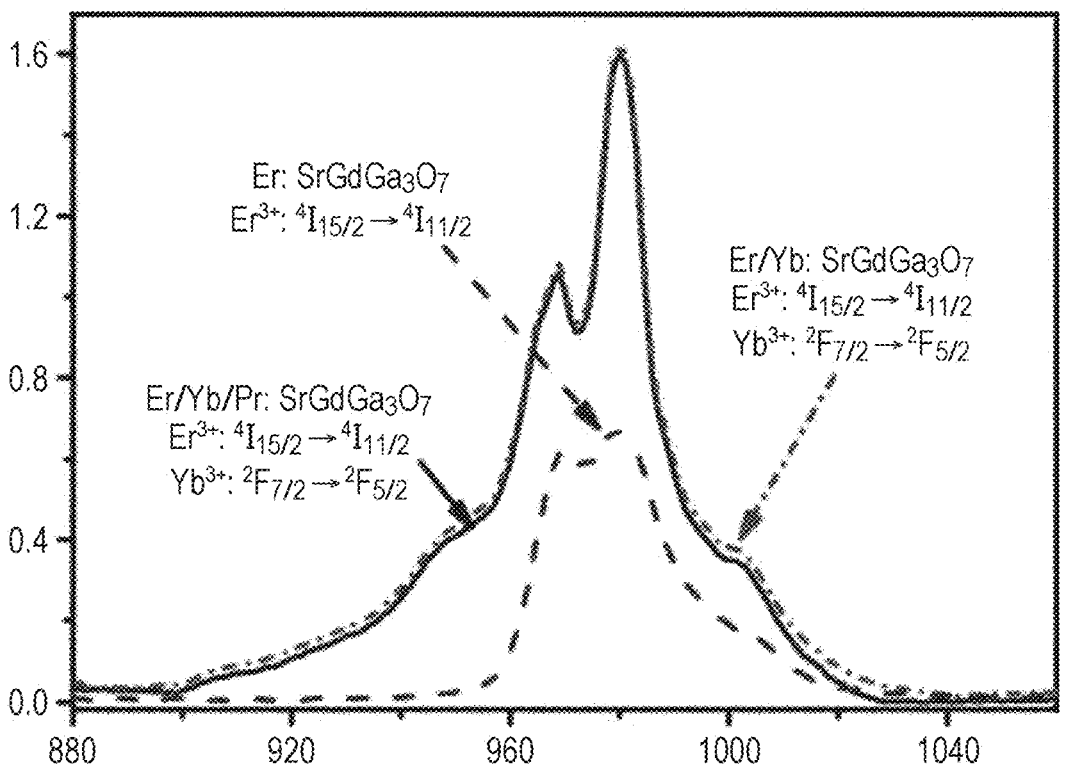
FIG. 10 is a diagram illustrating an excitation spectrum of a rare earth ion-containing ceramic nanoparticle probe (OTN ceramic probe Y) which is a second fluorescence substance in the third embodiment of the present invention.
Figure 11:
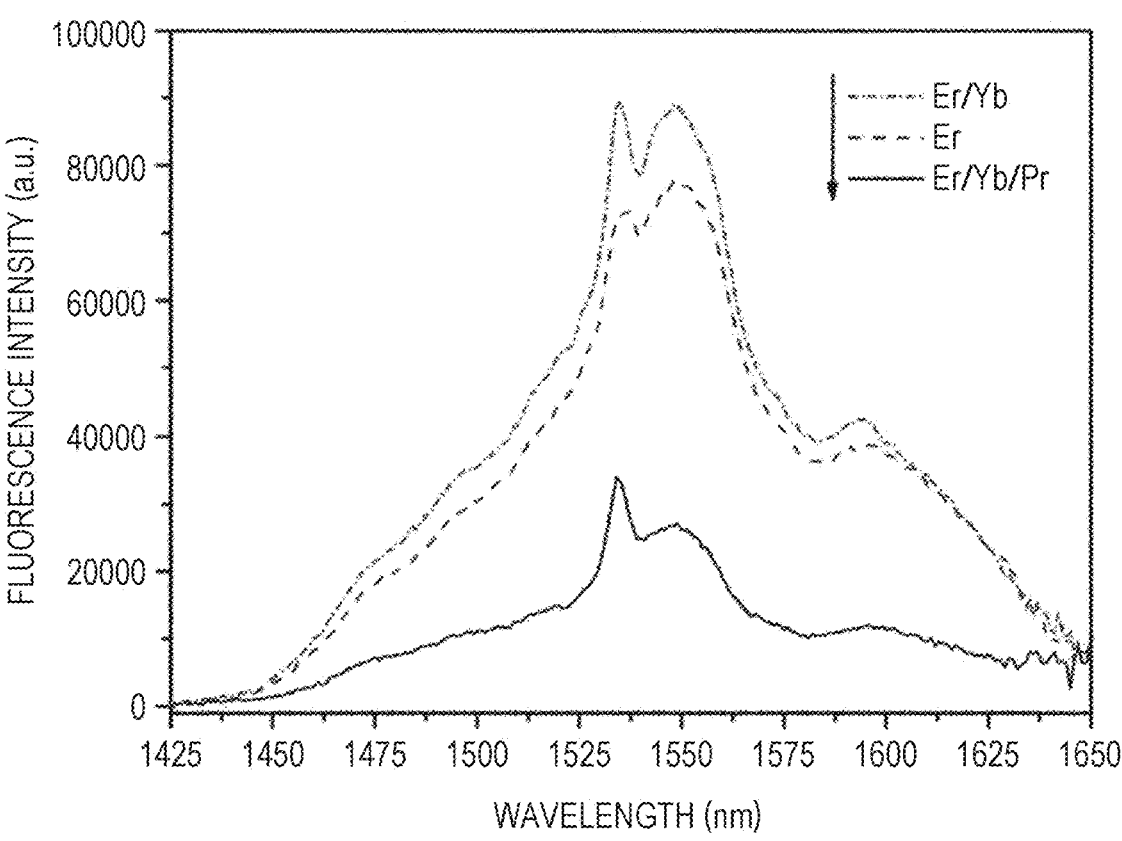
FIG. 11 is a diagram illustrating a fluorescence spectrum of a rare earth ion-containing ceramic nanoparticle probe (OTN ceramic probe Y) which is a second fluorescence substance in the third embodiment of the present invention.

FIG. 10 (source: FIG. 2 of "Evaluation of spectroscopic properties of Er(3+)/Yb(3+)/Pr(3+): SrGdGa3O7 crystal for use in mid-infrared lasers", Scientific Reports, September 2015) illustrates an excitation spectrum and a fluorescence spectrum of OTN ceramic probe Y which is the second fluorescence substance in the present embodiment. OTN ceramic probe Y is a kind of rare earth ion-containing ceramic nanoparticle probe. The maximum wavelength of the excitation wavelength of OTN ceramic probe Y is 980 nm. FIG. 11 (source: "FIG. 4" of the same) illustrates a fluorescence spectrum of OTN ceramic probe Y. The wavelength range of the fluorescence wavelength is 1400 to 1650 nm.

The first laser in the present embodiment is a laser that generates light having a wavelength of 808 nm. The second laser in the present embodiment is a laser that generates light having a wavelength of 980 nm.

Figure 12:
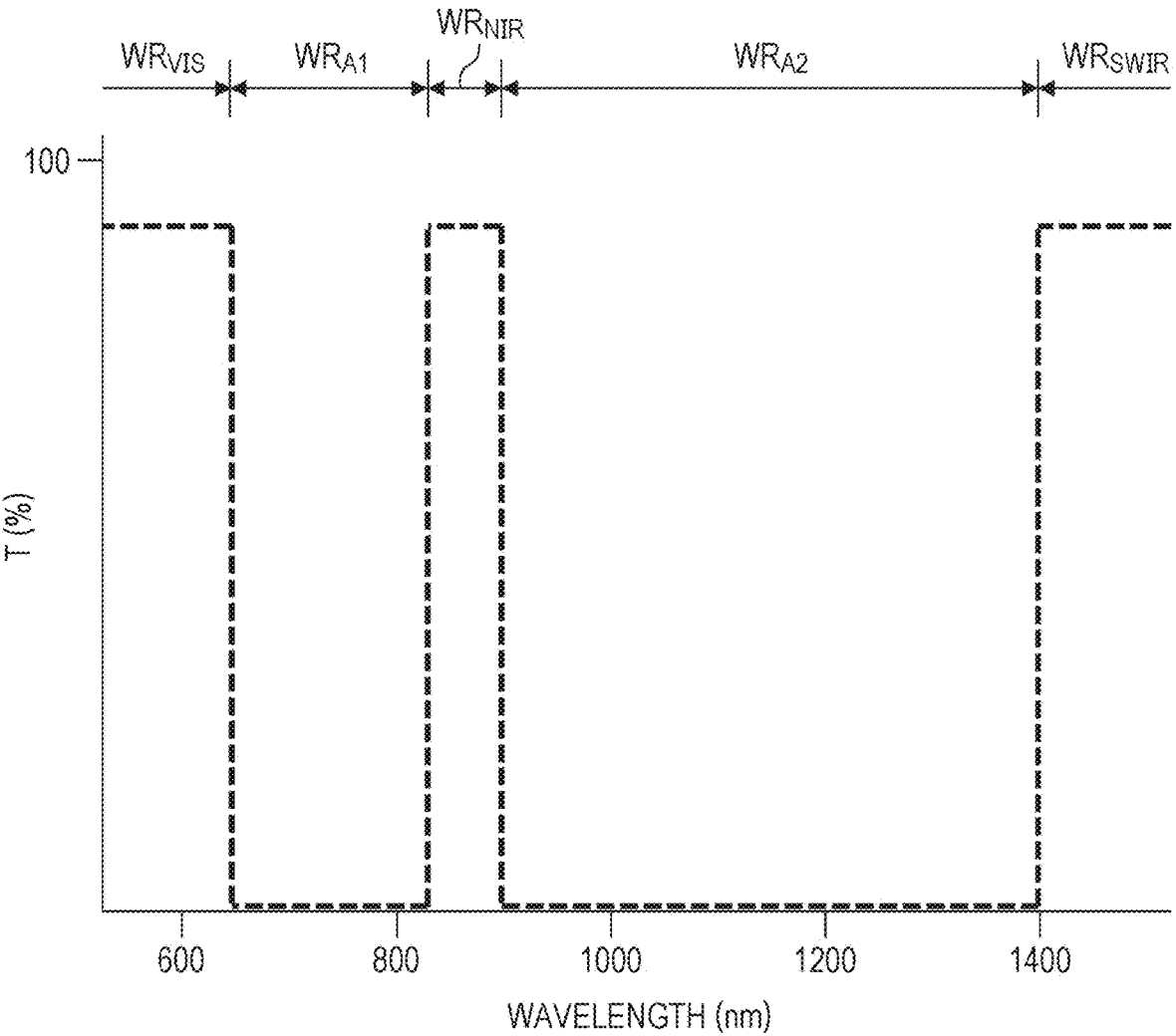
FIG. 12 is a diagram illustrating a transmission wavelength range and an attenuation wavelength range of a notch filter in the third embodiment of the present invention.

FIG. 12 illustrates a transmission wavelength range and an attenuation wavelength range of the notch filter in the present embodiment. The wavelength range in which the notch filter transmits light is such that $WR_{VIS}$ is 400 to 650 nm, $WR_{NIR}$ is 820 to 880 nm, and $WR_{SWIR}$ is 1400 to 1650 nm. In the wavelength range in which the notch filter attenuates light, $WR_{A1}$ is 650 to 820 nm and $WR_{A2}$ is 880 to 1400 nm.

In the present embodiment, a composite image in which an image of NIR fluorescence of ICG and an image of SWIR fluorescence of OTN ceramic probe Y are superimposed on a color VIS image can be formed. As described above, according to the present embodiment, as in the first embodiment, it is possible to detect fluorescence images of two kinds of fluorescence substances in an identifiable manner.

Therefore, as in first embodiment described above, even when two kinds of fluorescence substances having overlapping fluorescence wavelength ranges are used, in living body imaging in which sites detected by fluorescence can overlap, the sites labeled with the respective fluorescence substances can be clearly and distinguishably displayed.

In the present embodiment, the notch filter attenuates $WR_{A2}$ light having a wavelength range longer than a peak wavelength (835 nm) of NIR fluorescence of ICG and shorter than a peak wavelength (1530 nm) of SWIR fluorescence of OTN ceramic probe Y. Therefore, the distinction between the NIR fluorescence of ICG and the SWIR fluorescence of OTN ceramic probe Y becomes clearer, which is advantageous from the viewpoint of effectively using these fluorescence reagents.

Fourth Embodiment

The present embodiment is a mode for using Cy5.5 for the first fluorescence substance and ICG for the second fluorescence substance. The image forming apparatus of the present embodiment is substantially the same as that of the first embodiment described above except that the wavelength of the light of the first laser in the excitation light source and the transmitted light wavelength range and the attenuated light wavelength range in the notch filter are different.

Figure 13:
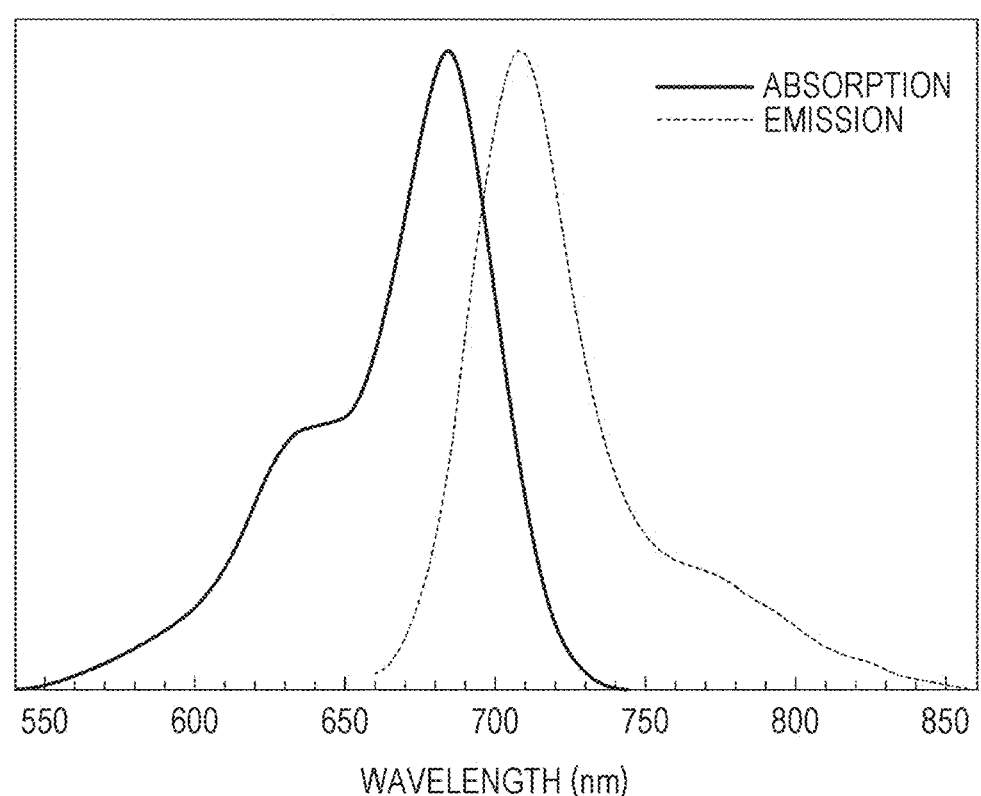
FIG. 13 is a diagram illustrating an excitation spectrum and a fluorescence spectrum of a Cy dye-labeled carboxylic acid (Cy5.5) which is a first fluorescence substance in the fourth embodiment of the present invention.

FIG. 13 (source: https://www.lumiprobe.com/p/cy55-nhs-ester) illustrates an excitation spectrum and a fluorescence spectrum of Cy5.5 which is the first fluorescence substance in the present embodiment. Cy5.5 is a kind of Cy dye-labeled carboxylic acid. The maximum wavelength of the excitation wavelength of Cy5.5 is 685 nm, and the wavelength range of the fluorescence wavelength is 660 to 850 nm.

The first laser in the present embodiment is a laser that generates light having a wavelength of 665 nm.

Figure 14:
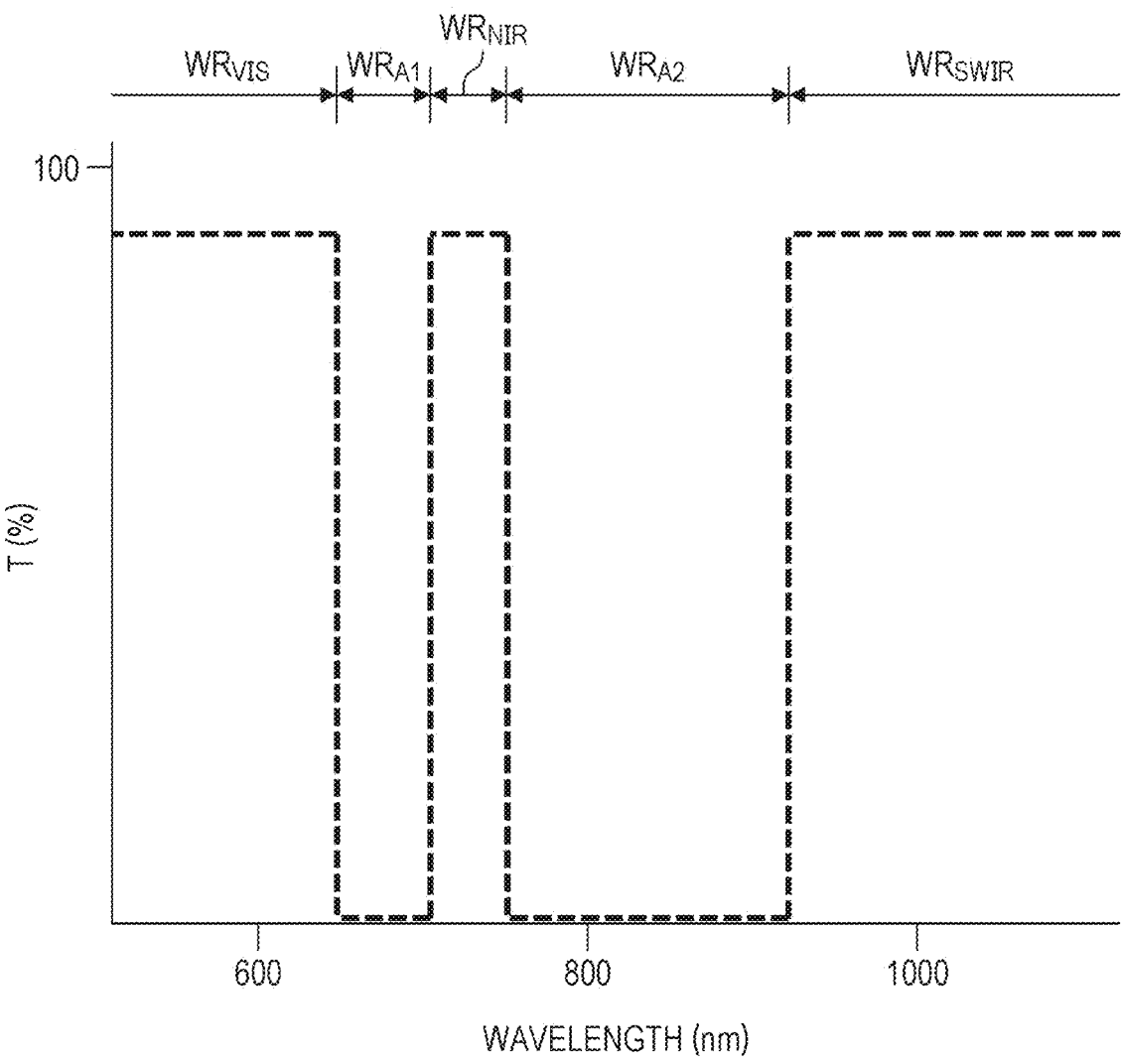
FIG. 14 is a diagram illustrating a transmission wavelength range and an attenuation wavelength range of a notch filter in the fourth embodiment of the present invention.

FIG. 14 illustrates a transmission wavelength range and an attenuation wavelength range of the notch filter in the present embodiment. The wavelength range in which the notch filter transmits light is such that $WR_{VIS}$ is 400 to 650 nm, $WR_{NIR}$ is 710 to 750 nm, and $WR_{SWIR}$ is 925 to 1300 nm. In the wavelength range in which the notch filter light attenuates, $WR_{A1}$ is 650 to 710 nm and $WR_{A2}$ is 750 to 925 nm.

In the present embodiment, a composite image in which an image of NIR fluorescence of Cy5.5 and an image of SWIR fluorescence of ICG are superimposed on a color VIS image can be formed. As described above, according to the present embodiment, as in the first embodiment, it is possible to detect fluorescence images of two kinds of fluorescence substances in an identifiable manner. Therefore, as in first embodiment described above, even when two kinds of fluorescence substances having overlapping fluorescence wavelength ranges are used, in living body imaging in which sites detected by fluorescence can overlap, the sites labeled with the respective fluorescence substances can be clearly and distinguishably displayed.

Fifth Embodiment

The present embodiment is a mode for using Cy5.5 for the first fluorescence substance and CH1055 for the second fluorescence substance. The image forming apparatus of the present embodiment is substantially the same as that of the first embodiment described above except that the wavelengths of the light of the first laser and the second laser in the excitation light source and the transmitted light wavelength range and the attenuated light wavelength range in the notch filter are different.

Figure 15:
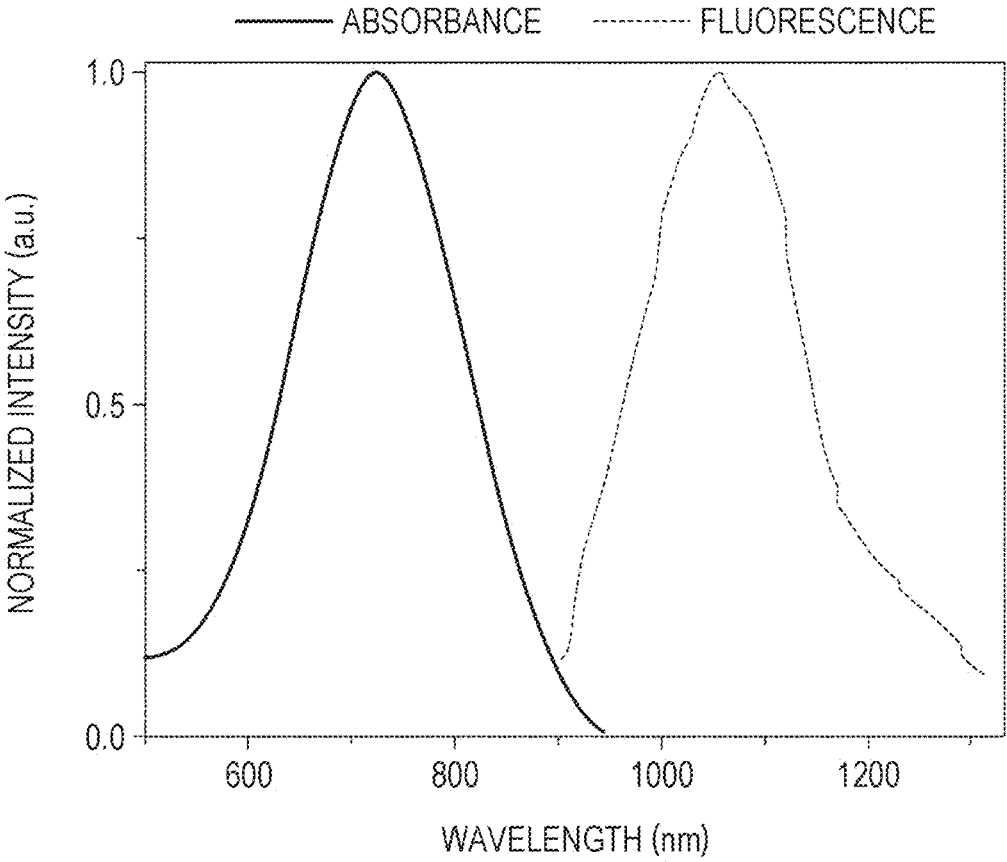
FIG. 15 is a diagram illustrating an excitation spectrum and a fluorescence spectrum of a D-A-D type dye (CH1055) which is a second fluorescence substance in the fifth embodiment of the present invention.

FIG. 15 (source: FIG. 16(B) of "Near-infrared dyes, nanomaterials and proteins", Chinese Chemical Letters 30, (2019), 1856-1882) illustrates an excitation spectrum and a fluorescence spectrum of CH1055 which is the second fluorescence substance in the present embodiment. CH1055 is a kind of donor-acceptor-donor (D-A-D) type dye. The maximum wavelength of the excitation wavelength of CH1055 is 750 nm, and the wavelength range of the fluorescence wavelength is 900 to 1350 nm.

The first laser in the present embodiment is a laser that generates light having a wavelength of 665 nm. The second laser in the present embodiment is a laser that generates light having a wavelength of 780 nm.

Figure 16:
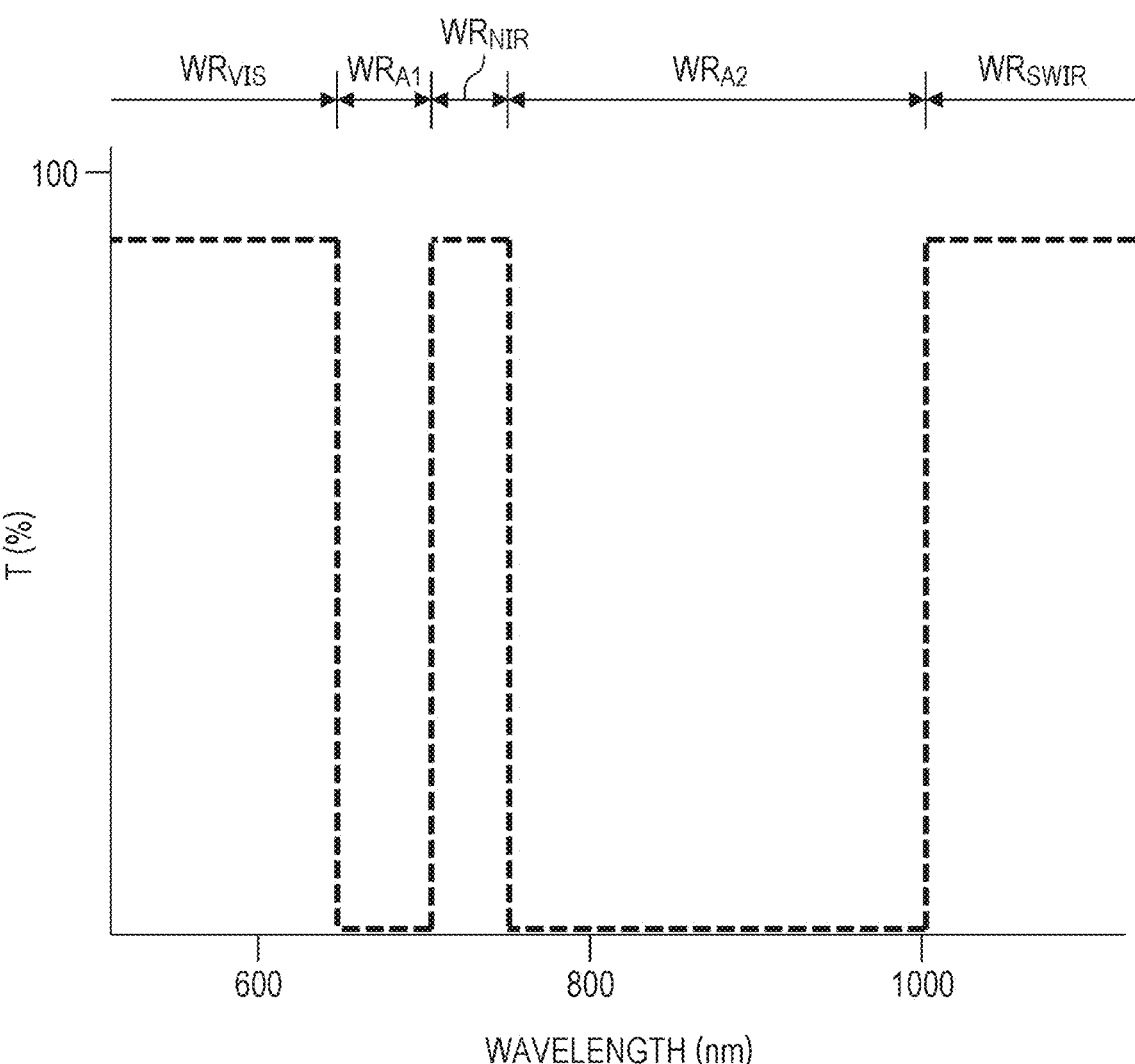
FIG. 16 is a diagram illustrating a transmission wavelength range and an attenuation wavelength range of a notch filter in the fifth embodiment of the present invention.

FIG. 16 illustrates a transmission wavelength range and an attenuation wavelength range of the notch filter in the present embodiment. The wavelength range in which the notch filter light transmits is such that $WR_{VIS}$ is 400 to 650 nm, $WR_{NIR}$ is 700 to 750 nm, and $WR_{SWIR}$ is 1000 to 1350 nm. In the wavelength range in which the notch filter light attenuates, $WR_{A1}$ is 650 to 700 nm and $WR_{A2}$ is 750 to 1000 nm.

In the present embodiment, a composite image in which an image of NIR fluorescence of Cy5.5 and an image of SWIR fluorescence of CH1055 are superimposed on a color VIS image can be formed. As described above, according to the present embodiment, as in the first embodiment, it is possible to detect fluorescence images of two kinds of fluorescence substances in an identifiable manner. Therefore, as in first embodiment described above, even when two kinds of fluorescence substances having overlapping fluorescence wavelength ranges are used, in living body imaging in which sites detected by fluorescence can overlap, the sites labeled with the respective fluorescence substances can be clearly and distinguishably displayed.

Sixth Embodiment

Figure 17:
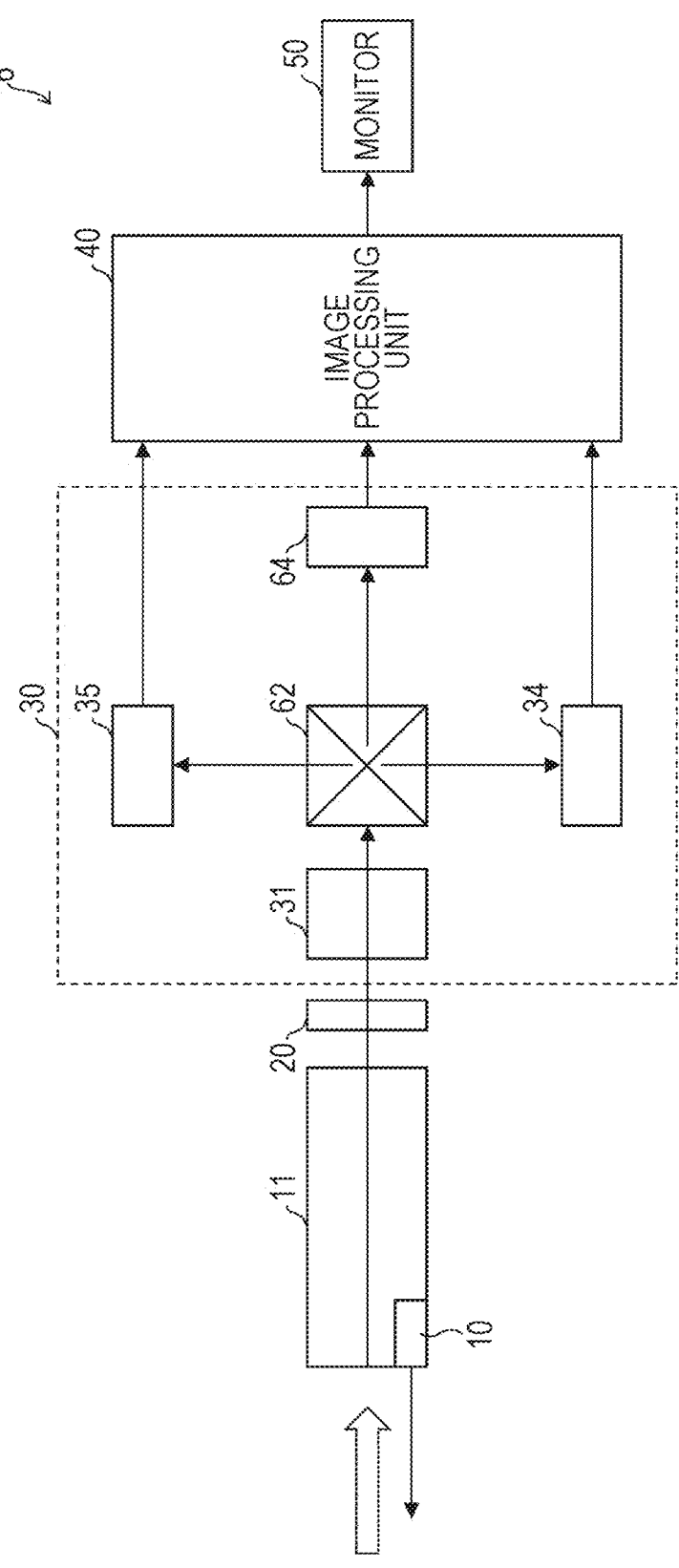
FIG. 17 is a diagram schematically illustrating a configuration of an image forming apparatus according to the sixth embodiment of the present invention.

The present embodiment is a mode for using CH1055 for the first fluorescence substance and OTN ceramic probe Y for the second fluorescence substance. In the image forming apparatus of the present embodiment, the wavelengths of the light of the first laser and the second laser in the excitation light source, the transmitted light wavelength range and the attenuated light wavelength range in the notch filter, and the beam splitter are different. In addition, an image forming apparatus 6 according to the present embodiment is substantially the same as the image forming apparatus 1 of the first embodiment described above except that, as illustrated in FIG. 17, a short wave infrared sensor 64 is included instead of the near infrared sensor 33. Similarly to the short wave infrared sensor 34, the short wave infrared sensor 64 is a monochrome image sensor having sensitivity to short wave infrared, and both of the short wave infrared sensors 34 and 64 are image sensors having sensitivity to a wavelength range of 400 to 1700 nm, for example.

The first laser in the present embodiment is a laser that generates light having a wavelength of 750 nm, and the second laser in the present embodiment is a laser that generates light having a wavelength of 980 nm. With reference to the quantum efficiency of OTN ceramic probe Y and the quantum yield of the CH1055, the output of the first laser is set to be larger than the output of the second laser so as to further reduce the intensity difference therebetween.

Figure 18:
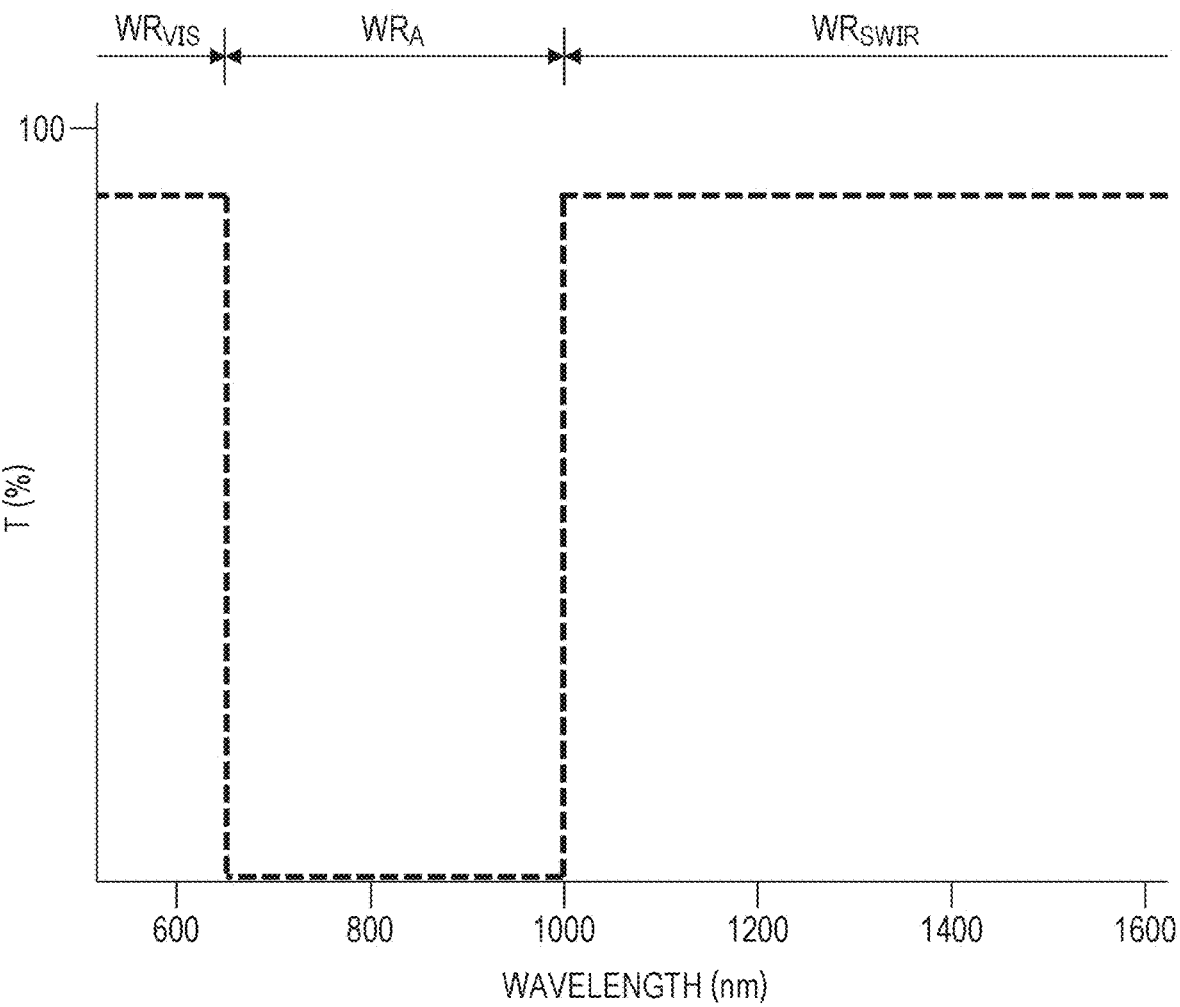
FIG. 18 is a diagram illustrating a transmission wavelength range and an attenuation wavelength range of a notch filter in the sixth embodiment of the present invention.

FIG. 18 illustrates a transmission wavelength range and an attenuation wavelength range of the notch filter in the present embodiment. The notch filter has a wavelength range for transmitting light in a wavelength range of visible light and a wavelength range of short wave infrared, and is designed to attenuate light in the wavelength range therebetween. That is, wavelength range $WR_{VIS}$ of visible light which the notch filter transmits is 400 to 650 nm, and wavelength range $WR_{SWIR}$ in which the notch filter transmits short wave infrared is 1000 to 1650 nm. The wavelength range $WR_A$ in which the notch filter attenuates light in is 650 to 1000 nm. The $WR_A$ substantially includes an excitation wavelength range (600 to 900 nm) of CH1055 and an excitation wavelength range (920 to 1020 nm) of OTN ceramic probe Y. The $WR_{SWIR}$ substantially includes a fluorescence wavelength range (900 to 1350 nm) of CH1055 and a fluorescence wavelength range (1400 to 1650 nm) of OTN ceramic probe Y.

The beam splitter 62 is a beam splitter that divides light in the wavelength range of the transmitted light set by the notch filter 20 into different directions, and is, for example, a cubic beam splitter having two types of optical thin films orthogonal to each other. Of the light that has passed through the notch filter 20 and the image forming lens 31, a beam splitter 62 guides visible light (400 to 650 nm) in one direction orthogonal to the incident direction, guides short wave infrared (900 to 1350 nm) in the other direction orthogonal to the incident direction, and transmits (straightly advances) short wave infrared (1400 to 1700 nm).

In the present embodiment, an image of the SWIR fluorescence of OTN ceramic probe Y is captured by the short wave infrared sensor 34, an image of the SWIR fluorescence of the CH1055 is captured by the short wave infrared sensor 64, and a composite image in which these SWIR fluorescence images are superimposed on a color VIS image can be formed. As described above, according to the present embodiment, as in the first embodiment, it is possible to detect fluorescence images of two kinds of fluorescence substances in an identifiable manner. Therefore, as in first embodiment described above, even when two kinds of fluorescence substances having overlapping fluorescence wavelength ranges are used, in living body imaging in which sites detected by fluorescence can overlap, the sites labeled with the respective fluorescence substances can be clearly and distinguishably displayed.

Seventh Embodiment

Figure 19:
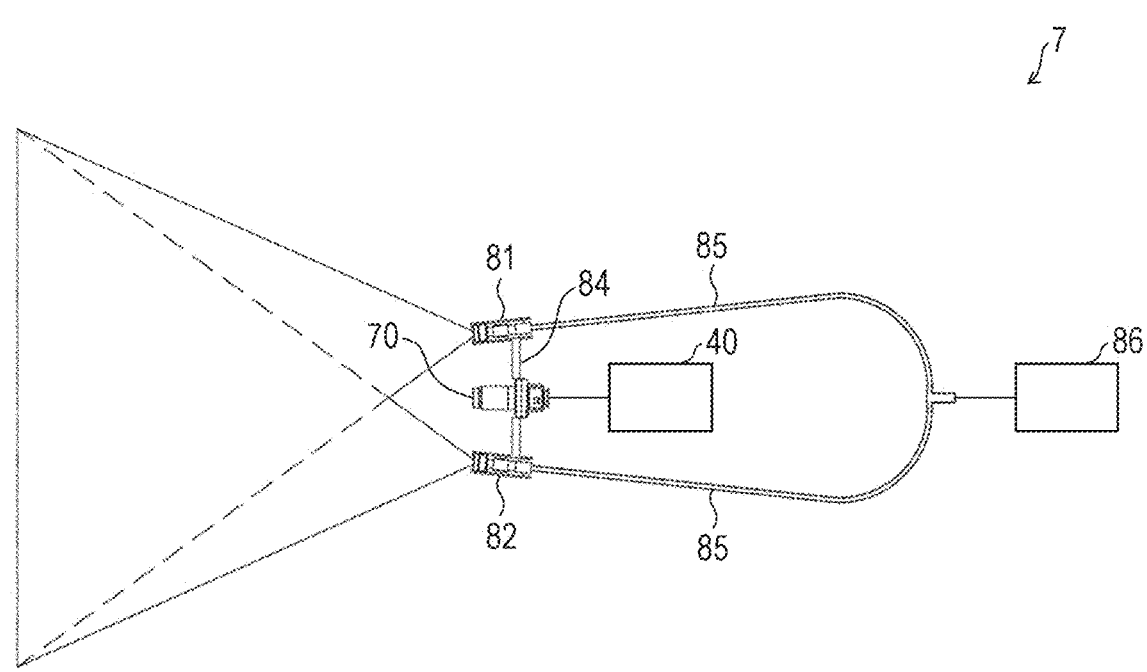
FIG. 19 is a diagram schematically illustrating an overall configuration of an image forming apparatus according to the seventh embodiment of the present invention.

FIG. 19 schematically illustrates an overall configuration of an image forming apparatus according to the seventh embodiment of the present invention. The present embodiment is a form in which the present invention is applied to an exoscope. As illustrated in FIG. 19, the image forming apparatus 7 does not include a radiation probe 11, and has substantially the same configuration as that of the first embodiment described above except that positions of an excitation light source, an image forming lens, and a notch filter of an imaging unit are different.

The image forming apparatus 7 includes an excitation light source, an imaging unit 70, and an image processing unit 40. The excitation light source includes excitation light diffusion lenses 81 and 82, a connection cable 85 connected to the excitation light diffusion lenses 81 and 82, and an excitation light adjustment unit 86 connected to the connection cable 85. The excitation light adjustment unit 86 includes a first laser and a second laser. The first laser outputs light having a wavelength of 660 nm, which is excitation light of MB, and the second laser outputs light having a wavelength of 808 nm, which is excitation light of ICG. The light output by the first laser is transmitted to the excitation light diffusion lens 81 through the connection cable 85, and the light output by the second laser is transmitted to the excitation light diffusion lens 82 through the connection cable 85. Each of the excitation light diffusion lenses 81 and 82 is supported by a frame 84 toward a target, and is configured to irradiate the target with light having a wavelength of 660 nm and light having a wavelength of 808 nm.

Figure 20:
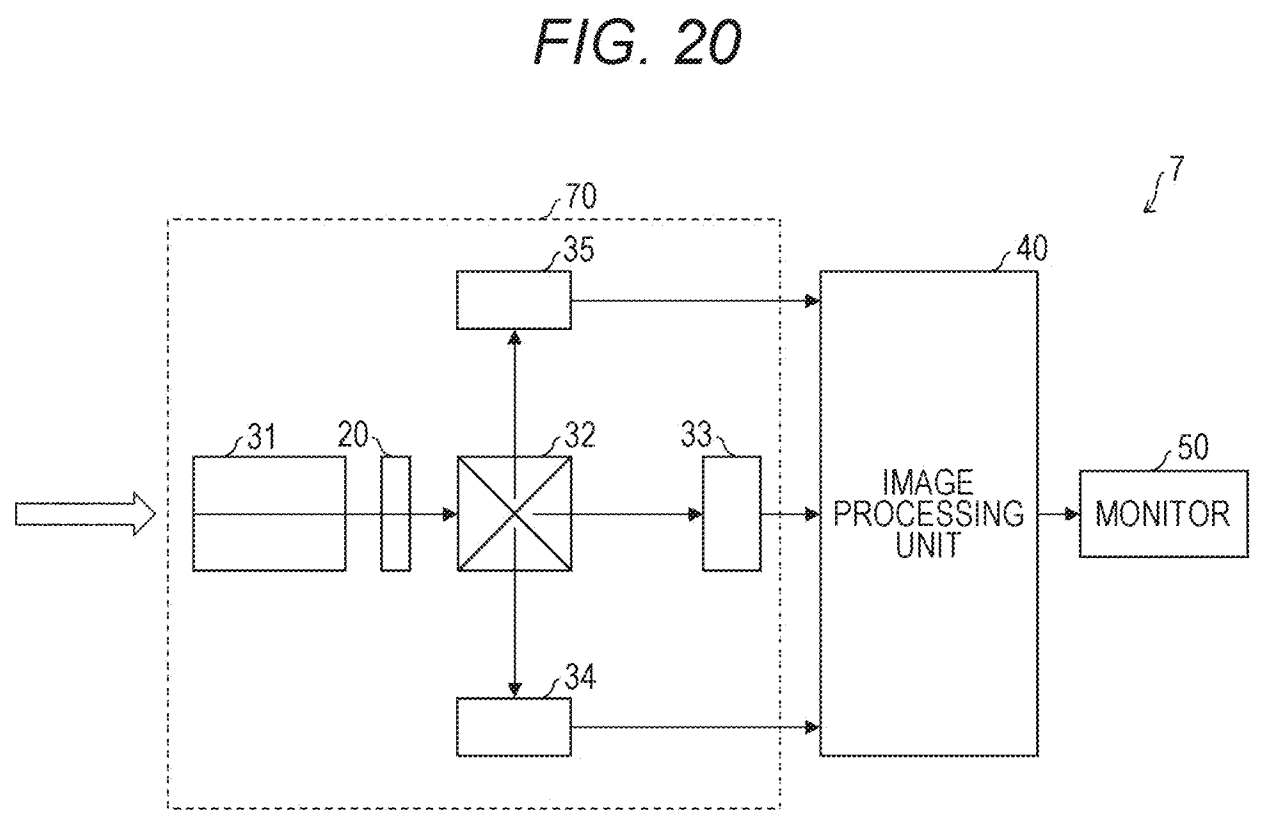

The imaging unit 70 is supported by the frame 84 toward a target. FIG. 20 schematically illustrates a functional configuration of the image forming apparatus 7 according to the present embodiment. As illustrated in FIG. 20, the imaging unit 70 includes an image forming lens 31, a notch filter 20, and a beam splitter 32 in this order from the object (target) side, and includes a near infrared sensor 33, a short wave infrared sensor 34, and a visible light sensor 35 close to the image plane of the beam splitter 32. Each sensor is connected to the image processing unit 40. The notch filter 20 is thus disposed in the imaging unit 70.

Figure 21:
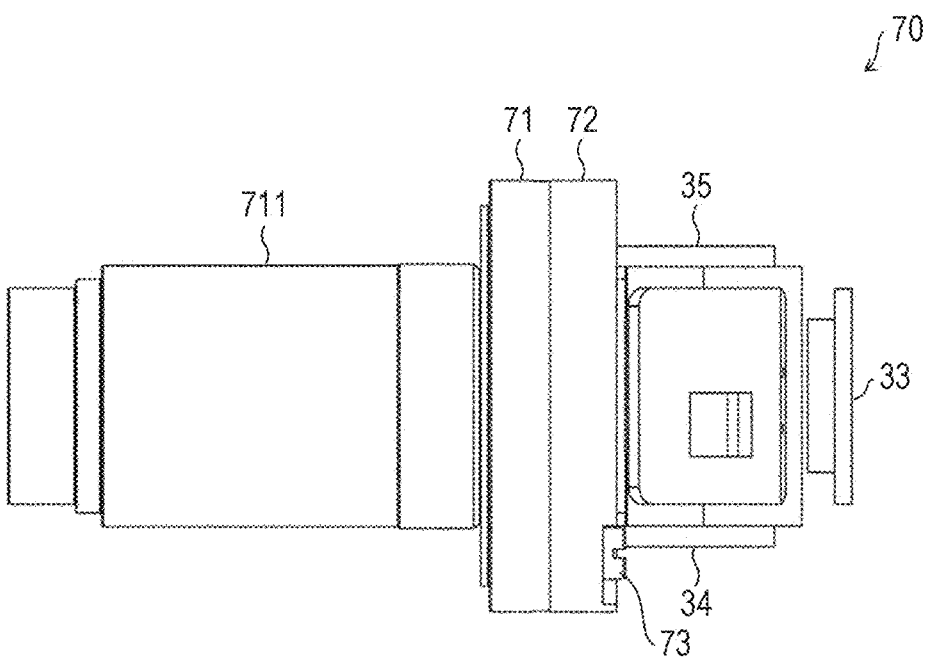
FIG. 21 is a plan view schematically illustrating an imaging unit in the seventh embodiment of the present invention.
Figure 22:
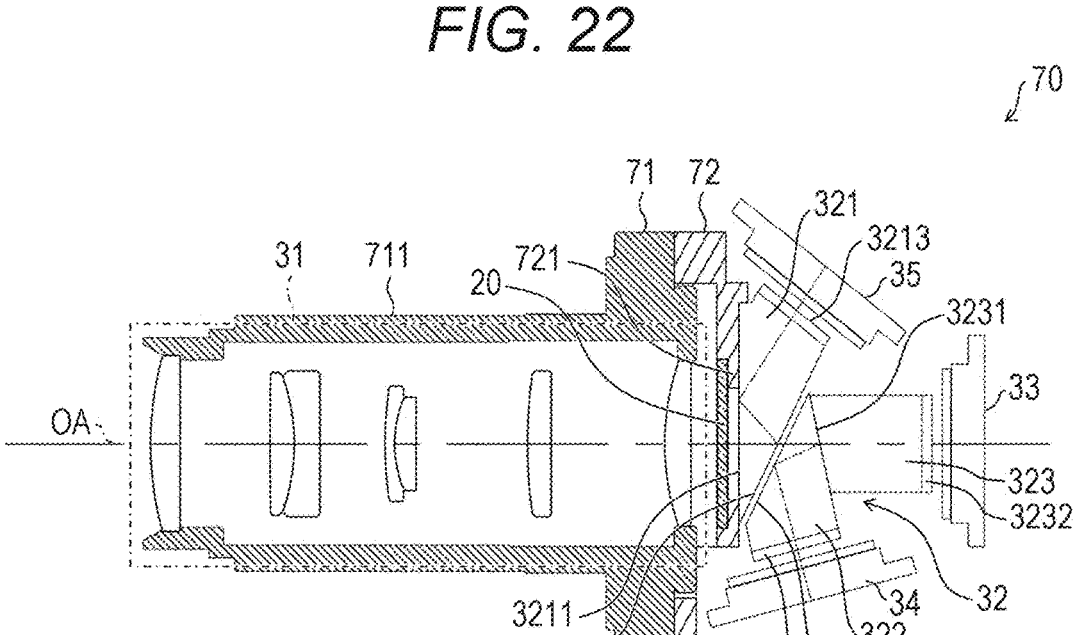
FIG. 22 is a cross-sectional view schematically illustrating an imaging unit in the seventh embodiment of the present invention.

A plan view of the imaging unit 70 is schematically illustrated in FIG. 21. As illustrated in FIG. 21, the imaging unit 70 includes a first adapter 71, a second adapter 72, and a screw 73 for fixing the first adapter 71 and the second adapter 72. The first adapter 71 includes a lens barrel 711, and the lens barrel 711 includes a plurality of lenses on the optical axis OA. In the present embodiment, the image forming lens 31 includes the plurality of lenses. The second adapter 72 includes the notch filter 20, the beam splitter 32, the near infrared sensor 33, the short wave infrared sensor 34, and the visible light sensor 35. The notch filter 20 is fitted into a recess 721 formed in the second adapter 72 and disposed on the optical axis OA.

The beam splitter 32 is disposed on one optical axis (optical axis OA), and includes three prisms 321, 322, and 323 made of the same glass material. Each of the three prisms 321, 322, and 323 is a trapezoidal prism obtained by cutting one end of a right angle prism.

The prism 321 includes a total reflection face 3211 and a first dielectric multilayer film 3212. The total reflection face 3211 is a face corresponding to the oblique side of the trapezoid in the prism 321, and the prism 321 is disposed in orientation in which the total reflection face 3211 is orthogonal to the optical axis OA. The first dielectric multilayer film 3212 is a film that is formed on a face corresponding to the base of the trapezoid in the prism 321 and reflects visible light in incident light. The visible light sensor 35 is disposed close to the image plane of the prism 321, and a short pass filter 3213 is disposed between the prism 321 and the visible light sensor 35. The short pass filter 3213 is an optical element that transmits light having a wavelength equal to or less than a boundary (that is, visible light components) with 650 nm as a boundary between visible light, and near infrared light and short wave infrared light, and blocks transmission of light having a wavelength exceeding the boundary (that is, components of near infrared light and short wave infrared light).

The prism 322 includes a total reflection face 3221. The total reflection face 3221 is a face corresponding to the oblique side of the trapezoid in the prism 322, and the prism 322 is disposed in orientation in which the total reflection face 3221 faces the first dielectric multilayer film 3212 of the prism 321 and intersects the optical axis OA. A gap (air gap) is provided between the prism 321 and the prism 322 in order to sufficiently realize the total reflection in the prism 322. A distance of the air gap is, for example, 5 to 15 μm. The short wave infrared sensor 34 is disposed close to the image plane of prism 322, and a long pass filter 3222 is disposed between the prism 322 and the short wave infrared sensor 34. The long pass filter 3222 has characteristics opposite to those of the short pass filter 3213. That is, the long pass filter 3222 is an optical element that transmits light (that is, a component of short wave infrared light) having a wavelength equal to or longer than a boundary of 925 nm, which is a boundary between visible light, and near infrared light and short wave infrared light, and blocks transmission of light (that is, components of visible light and near infrared light) having a wavelength below the boundary.

The prism 323 includes a second dielectric multilayer film 3231. The second dielectric multilayer film 3231 is formed on a face corresponding to the oblique side of the trapezoid in the prism 323, and the prism 323 is disposed in an orientation in which the face having the second dielectric multilayer film 3231 contacts a face corresponding to the base of the trapezoid of the prism 322 and intersects with the optical axis OA. The second dielectric multilayer film 3231 is a film that reflects short wave infrared light in incident light. The near infrared sensor 33 is disposed close to the image plane of the prism 323, and a bandpass filter 3232 is disposed between the prism 323 and the near infrared sensor 33. The bandpass filter 3232 is an optical element that selectively transmits light of 700 to 880 nm, which is a component of near infrared light, and blocks transmission of light of other wavelengths (that is, components of visible light and short wave infrared light).

The light reaching the prism 321 passes through the total reflection face 3211 and reaches the first dielectric multilayer film 3212. The visible light component of the reached light is reflected by the first dielectric multilayer film 3212, then reflected by the total reflection face 3211, reaches the visible light sensor 35 via the short pass filter 3213, and is detected. With such a configuration, mixing of components of near infrared light and short wave infrared light into components of visible light reaching the visible light sensor 35 is suppressed, and color reproducibility of a visible light image is improved.

The components of the near infrared light and the short wave infrared light transmitted through prism 321 are incident on the prism 322. The short wave infrared light component among the incident light components is reflected by the second dielectric multilayer film 3231 forming the interface between the prism 322 and the prism 323, then reflected by the total reflection face 3221, reaches the short wave infrared sensor 34 via the long pass filter 3222, and is detected. With such a configuration, it is possible to suppress mixing of the components of the visible light and the near infrared light into the components of the short wave infrared light reaching the short wave infrared sensor 34.

The component of the near infrared light transmitted through the second dielectric multilayer film 3231 and incident on the prism 323 reaches the near infrared sensor 33 via the bandpass filter 3232 and is detected. With such a configuration, it is possible to suppress mixing of components of visible light and short wave infrared light into components of near infrared light reaching the near infrared sensor 33.

Figure 23:
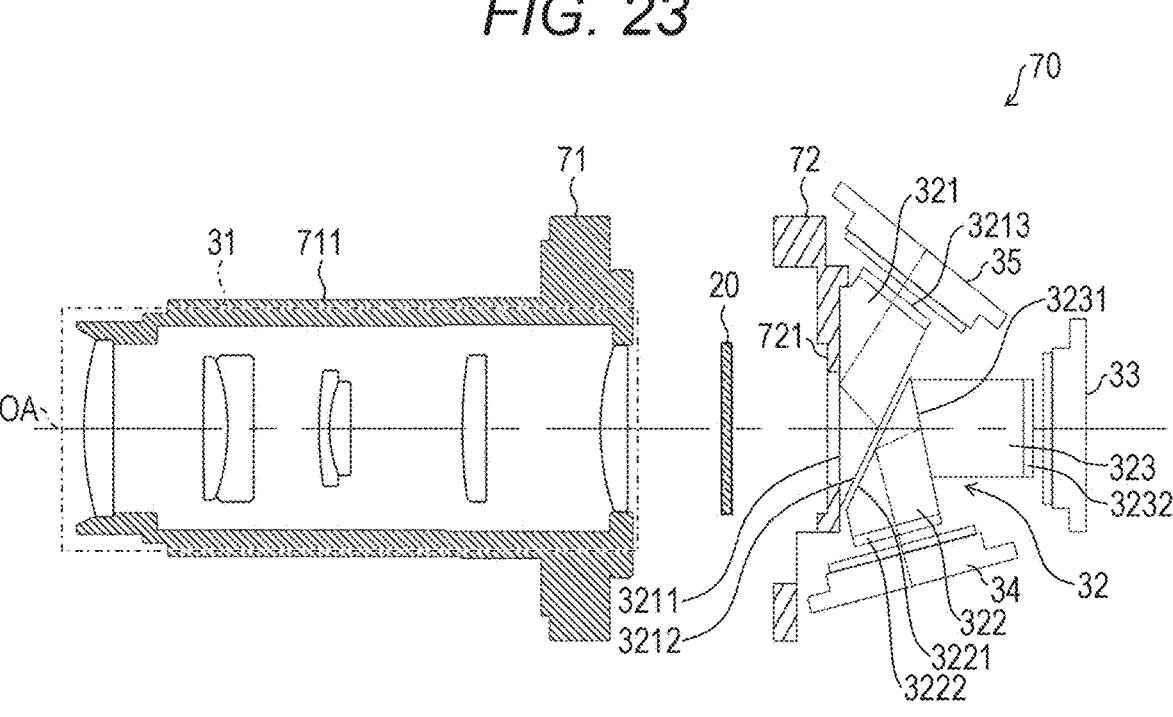
FIG. 23 is a cross-sectional view schematically illustrating a state in which an imaging unit in the seventh embodiment of the present invention is disassembled.

FIG. 23 is a cross-sectional view schematically illustrating an exploded state of imaging unit 70. By loosening and removing the screw 73, the imaging unit 70 is disassembled into the first adapter 71 and the second adapter 72. The notch filter 20 is simply fitted in the recess 721, and thus is easily detachable and replaceable.

When the image forming apparatus 7 is used, the object is irradiated with light having a wavelength of 660 nm from the excitation light diffusion lens 81, the object is irradiated with light having a wavelength of 808 nm from the excitation light diffusion lens 82, and the object is illuminated with visible light from an indoor lamp. The imaging range of the image forming lens 31 in the object is irradiated with the excitation light and the visible light substantially or completely overlapping.

The return light from the object passes through the image forming lens 31, reaches the notch filter 20, and passes through the beam splitter 32. The notch filter 20 transmits components of visible light, near infrared light, and short wave infrared light in the return light. As described above, the beam splitter 32 causes the visible light component in the return light to reach the visible light sensor 35, the short wave infrared light component in the return light to reach the short wave infrared sensor 34, and the near infrared light component in the return light to reach the near infrared sensor 33. The image data acquired by the imaging unit 70 is processed by the image processing unit 40, and is provided to the user of the image forming apparatus 7 by being displayed on, for example, the monitor 50.

Note that, in the present embodiment, the image forming apparatus 7 does not include a light source of visible light. This is because, in a case where the image forming apparatus 7 is in the form of an exoscope, illumination such as an indoor lamp that illuminates a target such as an inspection target person or a surgical shadowless lamp usually exists, and the illumination can be used as a light source of visible light. Therefore, the image forming apparatus 7 may further include a light source of visible light as the excitation light source. The light source of visible light may be fixed to, for example, the lens barrel 711 of the imaging unit 70 in a direction along the optical axis OA.

Furthermore, in the present embodiment, the position of the notch filter 20 in the optical system of the present embodiment may be any position closer to the object than the beam splitter 32. For example, the notch filter 20 may be disposed closest to the object in the optical system, and may be disposed at the distal end of the lens barrel while being held by the lens adapter, for example. Such an embodiment is also preferable from the viewpoint of easily performing attachment/detachment and replacement of the notch filter 20.

Furthermore, in the embodiment of the present invention, the arrangement of each of the sensors 33, 34, and 35 of the imaging unit can be appropriately changed within a range in which the effect of the present invention can be obtained. For example, in the seventh embodiment, a dielectric multilayer film that reflects a short wave infrared light component and transmits a visible light component and a near infrared light component may be formed on the prism 321, a dielectric multilayer film that reflects a near infrared light component and transmits a visible light component may be formed on the interface between the prism 322 and the prism 323, a sensor that detects the component reflected by the dielectric multilayer film may be disposed close to the image plane of the dielectric multilayer film, and the visible light sensor 35 may be disposed close to the image plane of the beam splitter 32 on the optical axis OA. As described above, in the embodiment of the present invention, the arrangement of each sensor can be appropriately changed by appropriately designing the prism shape and the dielectric multilayer film of the beam splitter.

Further, in the seventh embodiment, the beam splitter 32 is configured by the arrangement of three prisms appropriately including the dielectric multilayer film, but the form of the beam splitter is not limited in the embodiment of the present invention. That is, the beam splitter 32 in the seventh embodiment may be applied to another embodiment, and the cubic beam splitter in another embodiment may be applied to the seventh embodiment.

Other Embodiments

The image forming apparatus according to the present invention can be applied to living body imaging using two specific fluorescence substances applicable to a living body by appropriately setting an excitation light source and optical characteristics of a notch filter. The two specific fluorescence substances are two kinds of fluorescence substances having a wavelength range of fluorescence in which only one of the fluorescence substances is detected in near infrared and short wave infrared. Examples of fluorescence substances other than the fluorescence substances illustrated in the above-described embodiments and usable for the first fluorescence substance or the second fluorescence substance when the present invention is applied to living body imaging are illustrated in Table 3 below.

TABLE 3

| Fluorescence substance | Excitation wavelength (nm) | | Fluorescence wavelength (nm) | |
|---|---|---|---|---|
| | Maximum wavelength | Wavelength range | Maximum wavelength | Wavelength range |
| Cy5 | 643 | 550-670 | 667 | 620-800 |
| Flav7 | 1027 | 750-1100 | 1053 | 950-1350 |
| IR1061 | 1072 | 600-1100 | 1100 | 1000-1700 |
| BTC-1070 | 1014 | 800-1100 | 1070 | 900-1350 |
| Cytalux | — | 760~785 | — | 794~796 |
| BM104 | 685 | — | 705 | — |
| S0456 | 789 | — | 807 | — |
| ABY-029 | 776 | — | 792 | — |
| LS301 | 780 | — | 820 | — |
| ASP5354 | 780 | — | 820 | — |
| IRDye800CW | 773 | 550-820 | 792 | 750-1300 |

Modifications

In the present embodiment described above, the excitation light source and the light source of visible light may include an optical fiber that is optically connected to these light sources and guides light (excitation light and visible light) emitted from the light sources toward the object to be observed. This configuration is advantageous from the viewpoint of miniaturization of the light source.

The excitation light source may be a device that emits light having a single wavelength included in both the excitation wavelength range of the first fluorescence substance and the excitation wavelength range of the second fluorescence substance as excitation light for both the fluorescence substances. This configuration is advantageous from the viewpoint of simplification of the excitation light source.

The excitation light source may emit excitation light having a wavelength other than the maximum wavelength in the absorption wavelength range at least at one of the excitation wavelength of the first fluorescence substance and the excitation wavelength of the second fluorescence substance. This configuration is advantageous from the viewpoint of providing a sufficient difference in fluorescence intensity between the first fluorescence substance and the second fluorescence substance.

The optical filter unit may include a combination of two or more bandpass filters. This configuration is advantageous from the viewpoint that optical filter units corresponding to various combinations of the first fluorescence substance and the second fluorescence substance can be sequentially constructed.

The imaging unit may include a separation transmission filter unit that transmits light of two or more different wavelength ranges at a specific portion. Examples of the separation transmission filter unit include an NIR-SWIR filter in which an NIR filter unit that transmits near infrared light and a SWIR filter unit that transmits short wave infrared light are arranged in a checkered pattern, and a VIS-NIR-SWIR filter in which three types of a VIS filter unit that transmits visible light in addition to the NIR filter unit and the SWIR filter unit are arranged in a checkered pattern. This configuration is advantageous from the viewpoint of simplifying the configuration of the imaging unit since each of images of light in two or more different wavelength ranges can be imaged by a single imaging device.

In addition, the short wave infrared sensor may include a sensor having sensitivity from near infrared to short wave infrared. The short wave infrared sensor 34 instead of the near infrared sensor 33 may be adopted for such a short wave infrared sensor. This configuration is advantageous from the viewpoint that the type of the sensor can be further simplified, and an imaging unit that can cope with a combination of fluorescence substances in which any of fluorescence of the first fluorescence substance and fluorescence of the second fluorescence substance is short wave infrared fluorescence can be configured.

The function of the image processing unit 40 in the embodiment of the present invention is a program for causing a computer to function as the processing unit, and can be realized by a program for causing a computer to function as each control block of the processing unit.

In this case, the processing unit includes a computer that has at least one control device (for example, a processor) and at least one storage device (for example, a memory) as hardware for executing the program. The control device and the storage device execute the program to implement each function described in each of the above-described embodiments.

The program may be recorded on one or more non-transitory computer-readable recording media. This recording medium may or may not be included in the processing unit. In the latter case, the program may be supplied to the processing unit through any wired or wireless transmission medium.

In addition, some or all of the functions of the control blocks can be realized by a logic circuit. For example, an integrated circuit in which a logic circuit functioning as each control block is formed is also included in the scope of the present invention. In addition, for example, the functions of the control blocks can be realized by a quantum computer.

In addition, each processing described in above the embodiments may be executed by artificial intelligence (AI). In this case, the AI may operate in the control device, or may operate in another device (for example, an edge computer, a cloud server, or the like).

In addition, the image forming apparatus of the present invention may further include a diagnosis unit that diagnoses a tissue from the created composite image. The diagnosis unit may include a determination unit that determines an image by an image determination model that has learned the composite image data as teacher data. Examples of image determination models include neural networks and support vector machines. Examples of neural networks include convolutional neural networks (CNN), recurrent neural networks (RNN), and fully connected neural networks.

The image determination model can be trained with reference to teacher data. The teacher data includes image data of the composite image and at least one piece of information (such as a disease of a site) related to a site in the image corresponding to the image data. The learning of the image determination model can be created by preparing a sufficient number of pieces of the above teacher data (image data and information on a part corresponding thereto), causing the neural network to learn, and determining a path weight for each piece of image data. Examples of the algorithm for training the image determination model include backpropagation and ID3.

Note that the image determination model may be a model other than a model based on machine learning. For example, the image determination model may be a regression model having the above-described image data as an objective variable and information regarding appropriateness/inappropriateness of the image data as an explanatory variable.

The image processing unit 40 according to the embodiment of the present invention may perform processing of creating a composite image by boundary restoration processing in the processing of the fluorescence image. Even bright images (short wave side NIR image) should have definite boundary lines if the tissues are different, but the blurring of the images obscures the boundary lines between the tissues. On the other hand, although the signal of the dark image (SWIR image) is small, the boundary between tissues is clear. By extracting a boundary line with a dark image (SWIR image) and superimposing the obtained boundary line on a blurred image, it is possible to reproduce a clear boundary line between tissues originally possessed by the image.

For example, it is possible to use a dark image (SWIR image) with clear inter-tissue boundaries and apply a top-hat transform to this image. In this case, the image processing unit 40 selects a range of the SWIR image and creates an original image. The entire image can be divided into two regions according to the magnitude of the signal value of the tissue. For example, the region can be divided into a region of tissue emitting fluorescence of ICG (bright region) and a region of a portion outside the tissue (dark region).

Next, the image processing unit 40 creates an image obtained by expanding the original image. For example, at the boundary of the bright region, the image processing unit 40 copies the pixel value of the pixel adjacent to the boundary to a pixel outside the boundary adjacent to the boundary vertically and horizontally. As a result, a region (expansion region) expanded from the bright region by one pixel along the boundary is created.

Next, the image processing unit 40 creates an image of a boundary line from a difference between the original images before and after expansion. The bright region is subtracted from the expansion region, so that only the portion enlarged by the expansion remains. In this way, a boundary region corresponding to the boundary line of the tissue is created.

Next, the image processing unit 40 superimposes the boundary line image on the short wave side NIR image. For example, the image processing unit 40 superimposes an image obtained by multiplying the pixel value of the boundary region by a constant and emphasizing the boundary portion on the short wave side NIR image.

In this manner, by multiplying the signal of the boundary line obtained by applying the top-hat conversion to the dark image (SWIR image) by a constant and adding the signal to the bright image (short wave side NIR image) in which the boundary of the tissue is unclear, the clear boundary line between the tissues included in the dark image (SWIR image) is reflected in the bright image (short wave side NIR image). As a result, a bright image (composite image) in which a boundary between tissues is clear is combined.

Note that, in such image composition, the image in which the boundary portion is emphasized may be subtracted from the short wave side NIR image. Also in this case, a bright image (composite image) in which a boundary between tissues is clear is created.

In addition, the image processing unit 40 according to the embodiment of the present invention may perform processing of creating a composite image by performing processing of emphasizing an edge in processing of an image of fluorescence. For example, an image of a tissue emitting ICG fluorescence is taken as an original image.

First, the image processing unit 40 performs two-dimensional wavelet transformation on the SWIR image.

Next, the image processing unit 40 ranks high-pass components of the SWIR image. The edge component appears in the high-pass component. As described above, when the wavelet transform is performed on the dark image (SWIR image), the high-pass filter component corresponding to the edge has a large value.

Next, the image processing unit 40 selects high-pass image components of higher ranks of the SWIR image. A component having a large value is recorded in the high-pass filter.

Next, the image processing unit 40 performs two-dimensional wavelet transformation on the short wave side NIR image. For example, a wavelet transform is applied to a bright image (short wave side NIR image). In the bright image (short wave side NIR image) after the wavelet transform, since the short wave side NIR image is a high-luminance low-resolution image, the component corresponding to the edge becomes small and is buried in the component other than the edge.

Next, the image processing unit 40 multiplies the selected high-pass component (component having a large value recorded two processes earlier) of the SWIR image by a constant in the short wave side NIR image subjected to the wavelet transform. In this manner, the component in the short wave side NIR image subjected to the wavelet transform is restored using the wavelet transformed component of the SWIR image. As a result, a wavelet-transformed short wave side NIR image with definite edges is created.

Next, the image processing unit 40 performs inverse wavelet transformation on the short wave side NIR image that has been subjected to wavelet transformation and whose edges have been clarified. As a result, a composite image in which clear edges of a dark image (SWIR image) are reflected in a bright image (short wave side NIR image) is obtained.

Summary

A first aspect of the present invention is an image forming apparatus including an excitation light source (10) configured to irradiate an object (object to be observed) with excitation light for a first fluorescence substance (for example, MB) and excitation light for a second fluorescence substance (for example, ICG), an optical filter unit (notch filter 20) configured to transmit fluorescence in a first wavelength range including NIR or SWIR of the first fluorescence substance and fluorescence in a second wavelength range including SWIR of the second fluorescence substance from light from the object, an imaging unit (30) configured to capture each of an image of fluorescence in the first wavelength range and an image of fluorescence in the second wavelength range that have transmitted through the optical filter unit, and an image processing unit (40) configured to superimpose the image of fluorescence in the first wavelength range and the image of fluorescence in the second wavelength range in the imaging unit. According to the first aspect, it is possible to identifiably detect images of fluorescence of two kinds of fluorescence substances.

According to a second aspect of the present invention, in the first aspect, the optical filter unit attenuates light in a specific wavelength range longer than a peak wavelength of fluorescence in a first wavelength range of the first fluorescence substance and shorter than a peak wavelength of fluorescence in a second wavelength range of the second fluorescence substance. In the second aspect, since the attenuation wavelength range is located between the fluorescence in the first wavelength range and the fluorescence in the second wavelength range, overlapping of both types of fluorescence is further suppressed. Therefore, the second aspect is more effective from the viewpoint of clarifying the image of each fluorescence, and is more effective from the viewpoint of effectively using both fluorescence substances.

According to a third aspect of the present invention, in the first aspect or the second aspect, the optical filter unit attenuates light in a wavelength range longer than a wavelength of fluorescence with intensity of fluorescence in a first wavelength range in which intensity of fluorescence in the first wavelength range is larger than intensity of fluorescence in the second wavelength range. In the third aspect, between the first wavelength range and the second wavelength range, light having a higher fluorescence intensity in the first wavelength range is attenuated by the optical filter unit. Therefore, the third aspect is more effective from the viewpoint of further reducing the influence of the fluorescence in the first wavelength range on the fluorescence in the second wavelength range and from the viewpoint of improving the detection accuracy of the fluorescence in the second wavelength range.

According to a fourth aspect of the present invention, in any one of the first aspect to the third aspect, the optical filter unit is detachably provided in the image forming apparatus. In the fourth aspect, the optical filter unit can be replaced as appropriate, thereby making it possible to cope with various combinations of fluorescence substances. Therefore, the fourth aspect is more effective from the viewpoint of enhancing versatility and convenience of the image forming apparatus.

A fifth aspect of the present invention is a notch filter according to any one of the first aspect to the fourth aspect, in which the optical filter unit attenuates light in a first attenuation wavelength range shorter than the first wavelength range and light in a second attenuation wavelength range longer than the first wavelength range and shorter than the second wavelength range. In the fifth aspect, the optical filter unit can include a single notch filter, and the notch filter can be easily attached to and detached from the optical system of the image forming apparatus. Therefore, the fifth aspect is more effective from the viewpoint of simplification of the optical filter and the viewpoint of versatility of the image forming apparatus.

According to a sixth aspect of the present invention, in any one of the first aspect to the fifth aspect, the excitation light source irradiates the object with the excitation light by independently controlling the output of the excitation light for the first fluorescence substance and the output of the excitation light for the second fluorescence substance. In the sixth aspect, it is possible to further reduce a difference in intensity between fluorescence due to a difference in optical characteristics between fluorescence substances. Therefore, the sixth aspect is more effective from the viewpoint of aligning the distinguishability of the images of both types of fluorescence.

According to a seventh aspect of the present invention, in any one of the first aspect to the sixth aspect, the image processing unit includes a fluorescence image processing unit that processes an image of fluorescence in the first wavelength range and an image of fluorescence in the second wavelength range in images of different colors. In the seventh aspect, it is possible to more easily identify images of both types of fluorescence. Therefore, the seventh aspect is more effective from the viewpoint of enhancing distinguishability of images of both types of fluorescence.

According to an eighth aspect of the present invention, in any one of the first aspect to the seventh aspect, the optical filter unit further transmits visible light among light from the object, the imaging unit further captures an image of visible light that has transmitted through the optical filter unit, and the image processing unit further superimposes an image of visible light in the imaging unit on an image of fluorescence in the first wavelength range and an image of fluorescence in the second wavelength range. In the eighth aspect, since the composite image in which the images of both types of fluorescence are superimposed on the image of visible light is obtained, the positional relationship in the visual field of the site identified by both fluorescence substances becomes clearer. Therefore, the eighth aspect is more effective from the viewpoint of clearly indicating the position of the site identified by the fluorescence substance in the visual field.

According to a ninth aspect of the present invention, in any one of the first aspect to the eighth aspect, the image forming apparatus is an exoscope. The ninth aspect is more effective from the viewpoint of being easily applicable to image formation of a living body such as living body imaging.

According to the present invention, it is possible to clearly display a result of an examination using fluorescence in a living body. The present invention is expected to contribute to the achievement of, for example, Goal 3 of the sustainable development target (SDGs) proposed by the United Nations, "Health and welfare for all people".

The present invention is not limited to the above-described embodiments, and various modifications can be made within the scope of the claims. Embodiments obtained by combining as appropriate technical means disclosed in relation to different embodiments are also included in the technical scope of the present invention.

What is claimed is:
1. An image forming apparatus comprising:
an excitation light source configured to irradiate an object with excitation light for a first fluorescence substance and excitation light for a second fluorescence substance;
an optical filter configured to transmit, from light from the object, fluorescence in a first wavelength range including near infrared or short wave infrared of the first fluorescence substance and fluorescence in a second wavelength range including short wave infrared of the second fluorescence substance;

a sensor assembly configured to capture an image of fluorescence in the first wavelength range and an image of fluorescence in the second wavelength range that have transmitted through the optical filter; and an image processor configured to superimpose the image of the fluorescence in the first wavelength range and the image of the fluorescence in the second wavelength range in the sensor assembly, wherein the optical filter attenuates light in a specific wavelength range which is longer than a peak wavelength of fluorescence in the first wavelength range of the first fluorescence substance, has a peak wavelength of fluorescence in the second wavelength range of the second fluorescence substance and is shorter than the peak wavelength of fluorescence in the second wavelength range.

2. The image forming apparatus according to claim 1, wherein the optical filter attenuates light in a wavelength range longer than a wavelength of fluorescence with intensity of fluorescence in the first wavelength range in which intensity of fluorescence in the first wavelength range is larger than intensity of fluorescence in the second wavelength range.

3. The image forming apparatus according to claim 1, wherein the optical filter is detachably provided.

4. The image forming apparatus according to claim 1, wherein the optical filter is a notch filter that attenuates light in a first attenuation wavelength range shorter than the first wavelength range and light in a second attenuation wavelength range longer than the first wavelength range and shorter than the second wavelength range.

5. The image forming apparatus according to claim 1, wherein the excitation light source independently controls an output of excitation light for the first fluorescence substance and an output of excitation light for the second fluorescence substance to irradiate the object with the excitation light.

6. The image forming apparatus according to claim 1, wherein the image processor includes a fluorescence image processor configured to process an image of fluorescence in the first wavelength range and an image of fluorescence in the second wavelength range into images of different colors.

7. The image forming apparatus according to claim 1, wherein the optical filter further transmits visible light among light from the object, wherein the sensor assembly further captures an image of the visible light that has transmitted through the optical filter, and wherein the image processor further superimposes the image of the visible light in the sensor assembly on an image of fluorescence in the first wavelength range and an image of fluorescence in the second wavelength range.

8. The image forming apparatus according to claim 1, wherein the image forming apparatus is an exoscope.

* * * * *